(12) United States Patent
Wybo et al.

(10) Patent No.: US 10,870,002 B2
(45) Date of Patent: Dec. 22, 2020

(54) NEUROMUSCULAR SENSING DEVICE WITH MULTI-SENSOR ARRAY

(71) Applicant: Depuy Synthes Products, Inc., Raynham, MA (US)

(72) Inventors: Christopher Wybo, Brighton, MI (US); Aashish Shah, Ann Arbor, MI (US); Tarik Yardibi, Reading, MA (US); Emir Osmanagic, Norwell, MA (US); Darren Scarfe, LaSalle (CA)

(73) Assignee: Depuy Synthes Products, Inc., Raynham, MA (US)

( * ) Notice: Subject to any disclaimer, the term of this patent is extended or adjusted under 35 U.S.C. 154(b) by 71 days.

(21) Appl. No.: 16/158,734

(22) Filed: Oct. 12, 2018

(65) Prior Publication Data

US 2020/0114148 A1   Apr. 16, 2020

(51) Int. Cl.
 *A61N 1/00* (2006.01)
 *A61N 1/36* (2006.01)
 (Continued)

(52) U.S. Cl.
 CPC ........ *A61N 1/36003* (2013.01); *A61B 5/0488* (2013.01); *A61N 1/0452* (2013.01);
 (Continued)

(58) Field of Classification Search
 CPC .............. A61N 1/36003; A61N 1/0452; A61N 1/0476; A61N 1/0456; A61B 5/0488; A61B 5/4519; A61B 2505/05
 See application file for complete search history.

(56) References Cited

U.S. PATENT DOCUMENTS 3,200,814 A   8/1965 Taylor et al.
3,565,080 A   2/1971 Ide
(Continued)

FOREIGN PATENT DOCUMENTS

EP   1417000 A2   5/2004
EP   1575010 A1   9/2005
(Continued)

OTHER PUBLICATIONS

International search report on international application EP19202101.2.
(Continued)

*Primary Examiner* — Mallika D Fairchild
(74) *Attorney, Agent, or Firm* — Quinn IP Law

(57) ABSTRACT

A sensing device for detecting an artificially induced neuromuscular response within a limb of a subject includes a carrier material and a plurality of mechanical sensors. The carrier material is operative to be secured around a portion of the limb, and each of the plurality of mechanical sensors are coupled with the carrier material. Each mechanical sensor is positioned on the carrier material such that it is operative to monitor a mechanical response of a different muscle group of the limb. Each mechanical sensor then generates a respective mechanomyography output signal corresponding to the monitored mechanical response of its adjacent muscle group. These signals may then be communicated outbound from the device via communication circuitry provided on the device.

18 Claims, 10 Drawing Sheets

(51) Int. Cl.
*A61B 5/0488* (2006.01)
*A61N 1/04* (2006.01)
*A61B 5/00* (2006.01)

(52) U.S. Cl.
CPC .......... *A61N 1/0476* (2013.01); *A61B 5/4519* (2013.01); *A61B 2505/05* (2013.01); *A61N 1/0456* (2013.01)

(56) References Cited

U.S. PATENT DOCUMENTS

| | | | |
|---|---|---|---|
| 3,797,010 A | 3/1974 | Adler et al. | |
| 4,155,353 A | 5/1979 | Rea et al. | |
| 4,493,327 A | 1/1985 | Bergelson et al. | |
| 4,807,642 A | 2/1989 | Brown | |
| 4,817,628 A | 4/1989 | Zealear et al. | |
| 4,940,453 A | 7/1990 | Cadwell | |
| 4,994,015 A | 2/1991 | Cadwell | |
| 5,047,005 A | 9/1991 | Cadwell | |
| 5,078,674 A | 1/1992 | Cadwell | |
| 5,116,304 A | 5/1992 | Cadwell | |
| 5,178,145 A | 1/1993 | Rea | |
| 5,284,153 A | 2/1994 | Raymond et al. | |
| 5,284,154 A | 2/1994 | Raymond et al. | |
| 5,482,038 A | 1/1996 | Ruff | |
| 5,562,707 A * | 10/1996 | Prochazka | A61N 1/05 607/2 |
| 5,566,678 A | 10/1996 | Cadwell | |
| 5,593,429 A | 1/1997 | Ruff | |
| 5,631,667 A | 5/1997 | Cadwell | |
| 5,775,331 A | 7/1998 | Raymond et al. | |
| 5,860,939 A | 1/1999 | Wofford et al. | |
| 5,888,370 A | 3/1999 | Becker et al. | |
| 5,993,630 A | 11/1999 | Becker et al. | |
| 5,993,632 A | 11/1999 | Becker et al. | |
| 6,030,401 A | 2/2000 | Marino | |
| 6,093,205 A | 7/2000 | McLeod et al. | |
| 6,181,961 B1 | 1/2001 | Prass | |
| 6,183,518 B1 | 2/2001 | Ross et al. | |
| 6,206,921 B1 | 3/2001 | Guagliano et al. | |
| 6,221,082 B1 | 4/2001 | Marino et al. | |
| 6,224,603 B1 | 5/2001 | Marino | |
| 6,251,140 B1 | 6/2001 | Marino et al. | |
| 6,264,659 B1 | 7/2001 | Ross et al. | |
| 6,266,394 B1 | 7/2001 | Marino | |
| 6,266,558 B1 | 7/2001 | Gozani et al. | |
| 6,280,447 B1 | 8/2001 | Marino et al. | |
| 6,287,832 B1 | 9/2001 | Becker et al. | |
| 6,290,724 B1 | 9/2001 | Marino | |
| 6,312,443 B1 | 11/2001 | Stone | |
| 6,324,432 B1 | 11/2001 | Rigaux et al. | |
| 6,361,508 B1 | 3/2002 | Johnson et al. | |
| 6,368,325 B1 | 4/2002 | McKinley et al. | |
| 6,387,070 B1 | 5/2002 | Marino et al. | |
| 6,387,130 B1 | 5/2002 | Stone et al. | |
| 6,436,143 B1 | 8/2002 | Ross et al. | |
| 6,466,817 B1 | 10/2002 | Kaula et al. | |
| 6,478,805 B1 | 11/2002 | Marino et al. | |
| 6,485,518 B1 | 11/2002 | Cornwall et al. | |
| 6,491,626 B1 | 12/2002 | Stone et al. | |
| 6,500,128 B2 | 12/2002 | Marino | |
| 6,519,319 B1 | 2/2003 | Marino et al. | |
| 6,530,930 B1 | 3/2003 | Marino et al. | |
| 6,533,797 B1 | 3/2003 | Stone et al. | |
| 6,540,747 B1 | 4/2003 | Marino | |
| 6,564,078 B1 | 5/2003 | Marino et al. | |
| 6,613,007 B1 * | 9/2003 | Reid, Jr. | A61F 13/08 602/62 |
| 6,638,281 B2 | 10/2003 | Gorek | |
| 6,641,708 B1 | 11/2003 | Becker et al. | |
| 6,654,634 B1 | 11/2003 | Prass | |
| 6,739,112 B1 | 5/2004 | Marino | |
| 6,760,616 B2 | 7/2004 | Hoey et al. | |
| 6,764,452 B1 | 7/2004 | Gillespie et al. | |
| 6,764,489 B2 | 7/2004 | Ferree | |
| 6,802,844 B2 | 10/2004 | Ferree | |
| 6,805,668 B1 | 10/2004 | Cadwell | |
| 6,807,438 B1 | 10/2004 | Brun Del Re et al. | |
| 6,843,790 B2 | 1/2005 | Ferree | |
| 6,852,126 B2 | 2/2005 | Ahlgren | |
| 6,870,109 B1 | 3/2005 | Villarreal | |
| 6,887,248 B2 | 5/2005 | McKinley et al. | |
| 6,923,814 B1 | 8/2005 | Hildebrand et al. | |
| 6,945,973 B2 | 9/2005 | Bray | |
| 6,964,674 B1 | 11/2005 | Matsuura et al. | |
| 6,972,199 B2 | 12/2005 | Lebouitz et al. | |
| 6,981,990 B2 | 1/2006 | Keller | |
| 7,001,432 B2 | 2/2006 | Keller et al. | |
| 7,025,769 B1 | 4/2006 | Ferree | |
| 7,050,848 B2 | 5/2006 | Hoey et al. | |
| 7,072,521 B1 | 7/2006 | Cadwell | |
| 7,079,883 B2 | 7/2006 | Marino et al. | |
| 7,160,303 B2 | 1/2007 | Keller | |
| 7,162,850 B2 | 1/2007 | Marino et al. | |
| 7,166,113 B2 | 1/2007 | Arambula et al. | |
| 7,175,662 B2 | 2/2007 | Link et al. | |
| 7,177,677 B2 | 2/2007 | Kaula et al. | |
| 7,207,949 B2 | 4/2007 | Miles et al. | |
| 7,214,197 B2 | 5/2007 | Prass | |
| 7,214,225 B2 | 5/2007 | Ellis et al. | |
| 7,216,001 B2 | 5/2007 | Hacker et al. | |
| 7,230,688 B1 | 6/2007 | Villarreal | |
| 7,236,832 B2 | 6/2007 | Hemmerling et al. | |
| 7,267,691 B2 | 9/2007 | Keller et al. | |
| 7,296,500 B1 | 11/2007 | Martinelli | |
| 7,320,689 B2 | 1/2008 | Keller | |
| 7,338,531 B2 | 3/2008 | Ellis et al. | |
| 7,341,590 B2 | 3/2008 | Ferree | |
| 7,367,958 B2 | 5/2008 | McBean et al. | |
| 7,374,448 B1 | 5/2008 | Jepsen et al. | |
| 7,379,767 B2 | 5/2008 | Rea | |
| 7,470,236 B1 | 12/2008 | Kelleher et al. | |
| 7,485,146 B1 | 2/2009 | Crook et al. | |
| 7,522,953 B2 | 4/2009 | Kaula et al. | |
| 7,527,629 B2 | 5/2009 | Link et al. | |
| 7,527,649 B1 | 5/2009 | Blain | |
| 7,553,307 B2 | 6/2009 | Bleich et al. | |
| 7,555,343 B2 | 6/2009 | Bleich | |
| 7,569,067 B2 | 8/2009 | Keller | |
| 7,578,819 B2 | 8/2009 | Bleich et al. | |
| 7,582,058 B1 | 9/2009 | Miles et al. | |
| 7,583,991 B2 | 9/2009 | Rea | |
| 7,611,522 B2 | 11/2009 | Gorek | |
| 7,618,423 B1 | 11/2009 | Valentine et al. | |
| 7,628,813 B2 | 12/2009 | Link | |
| 7,634,315 B2 | 12/2009 | Cholette | |
| 7,657,308 B2 | 2/2010 | Miles et al. | |
| 7,664,544 B2 | 2/2010 | Miles et al. | |
| 7,666,195 B2 | 2/2010 | Kelleher et al. | |
| 7,668,588 B2 | 2/2010 | Kovacs | |
| 7,691,057 B2 | 4/2010 | Miles et al. | |
| 7,693,562 B2 | 4/2010 | Marino et al. | |
| 7,708,776 B1 | 5/2010 | Blain et al. | |
| 7,713,463 B1 | 5/2010 | Reah et al. | |
| 7,722,613 B2 | 5/2010 | Sutterlin et al. | |
| 7,722,673 B2 | 5/2010 | Keller | |
| 7,738,968 B2 | 6/2010 | Bleich | |
| 7,738,969 B2 | 6/2010 | Bleich | |
| 7,740,631 B2 | 6/2010 | Bleich et al. | |
| 7,766,816 B2 | 8/2010 | Chin et al. | |
| 7,776,049 B1 | 8/2010 | Curran et al. | |
| 7,776,094 B2 | 8/2010 | McKinley et al. | |
| 7,785,248 B2 | 8/2010 | Annest et al. | |
| 7,785,253 B1 | 8/2010 | Arambula et al. | |
| 7,815,682 B1 | 10/2010 | Peterson et al. | |
| 7,819,801 B2 | 10/2010 | Miles et al. | |
| 7,828,855 B2 | 11/2010 | Ellis et al. | |
| 7,833,251 B1 | 11/2010 | Ahlgren et al. | |
| 7,857,813 B2 | 12/2010 | Schmitz et al. | |
| 7,862,592 B2 | 1/2011 | Peterson et al. | |
| 7,862,614 B2 | 1/2011 | Keller et al. | |
| 7,867,277 B1 | 1/2011 | Tohmeh | |
| 7,883,527 B2 | 2/2011 | Matsuura et al. | |
| 7,887,538 B2 | 2/2011 | Bleich et al. | |

(56) References Cited

U.S. PATENT DOCUMENTS

| | | | |
|---|---|---|---|
| 7,887,568 B2 | 2/2011 | Ahlgren |
| 7,887,595 B1 | 2/2011 | Pimenta |
| 7,892,173 B2 | 2/2011 | Miles et al. |
| 7,901,430 B2 | 3/2011 | Matsuura et al. |
| 7,905,840 B2 | 3/2011 | Pimenta et al. |
| 7,905,886 B1 | 3/2011 | Curran et al. |
| 7,914,350 B1 | 3/2011 | Bozich et al. |
| 7,918,849 B2 | 4/2011 | Bleich et al. |
| 7,918,891 B1 | 4/2011 | Curran et al. |
| 7,920,922 B2 | 4/2011 | Gharib et al. |
| 7,927,337 B2 | 4/2011 | Keller |
| 7,935,051 B2 | 5/2011 | Miles et al. |
| 7,938,830 B2 | 5/2011 | Saadat et al. |
| 7,942,104 B2 | 5/2011 | Butcher et al. |
| 7,942,826 B1 | 5/2011 | Scholl et al. |
| 7,946,236 B2 | 5/2011 | Butcher |
| 7,959,577 B2 | 6/2011 | Schmitz et al. |
| 7,962,191 B2 | 6/2011 | Marino et al. |
| 7,963,915 B2 | 6/2011 | Bleich |
| 7,963,927 B2 | 6/2011 | Kelleher et al. |
| 7,981,058 B2 | 7/2011 | Akay |
| 7,981,144 B2 | 7/2011 | Geist et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,012,212 B2 | 9/2011 | Link et al. |
| 8,016,767 B2 | 9/2011 | Miles et al. |
| 8,016,776 B2 | 9/2011 | Bourget et al. |
| 8,027,716 B2 | 9/2011 | Gharib et al. |
| 8,048,080 B2 | 11/2011 | Bleich et al. |
| 8,050,769 B2 | 11/2011 | Gharib et al. |
| 8,055,349 B2 | 11/2011 | Gharib et al. |
| 8,062,298 B2 | 11/2011 | Schmitz et al. |
| 8,062,300 B2 | 11/2011 | Schmitz et al. |
| 8,062,369 B2 | 11/2011 | Link |
| 8,062,370 B2 | 11/2011 | Keller et al. |
| 8,063,770 B2 | 11/2011 | Costantino |
| 8,068,912 B2 | 11/2011 | Kaula et al. |
| 8,070,812 B2 | 12/2011 | Keller |
| 8,074,591 B2 | 12/2011 | Butcher et al. |
| 8,075,499 B2 | 12/2011 | Nathan et al. |
| 8,075,601 B2 | 12/2011 | Young |
| 8,083,685 B2 | 12/2011 | Fagin et al. |
| 8,083,796 B1 | 12/2011 | Raiszadeh et al. |
| 8,088,163 B1 | 1/2012 | Kleiner |
| 8,088,164 B2 | 1/2012 | Keller |
| 8,090,436 B2 | 1/2012 | Hoey et al. |
| 8,092,455 B2 | 1/2012 | Neubardt et al. |
| 8,092,456 B2 | 1/2012 | Bleich et al. |
| 8,103,339 B2 | 1/2012 | Rea |
| 8,114,019 B2 | 2/2012 | Miles et al. |
| 8,114,162 B1 | 2/2012 | Bradley |
| 8,123,668 B2 | 2/2012 | Annest et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,147,551 B2 | 4/2012 | Link et al. |
| 8,165,653 B2 | 4/2012 | Marino et al. |
| 8,167,915 B2 | 5/2012 | Ferree et al. |
| 8,172,750 B2 | 5/2012 | Miles et al. |
| 8,206,312 B2 | 6/2012 | Farquhar |
| 8,255,044 B2 | 8/2012 | Miles et al. |
| 8,255,045 B2 | 8/2012 | Gharib et al. |
| 8,303,515 B2 | 11/2012 | Miles et al. |
| 8,337,410 B2 | 12/2012 | Kelleher et al. |
| 8,343,065 B2 | 1/2013 | Bartol et al. |
| 8,343,079 B2 | 1/2013 | Bartol et al. |
| 8,394,129 B2 | 3/2013 | Morgenstern Lopez et al. |
| 8,500,653 B2 | 8/2013 | Farquhar |
| 8,500,738 B2 | 8/2013 | Wolf, II |
| 8,517,954 B2 | 8/2013 | Bartol et al. |
| 8,535,224 B2 | 9/2013 | Cusimano Reaston et al. |
| 8,538,539 B2 | 9/2013 | Gharib et al. |
| 8,556,808 B2 | 10/2013 | Miles et al. |
| 8,562,539 B2 | 10/2013 | Marino |
| 8,562,660 B2 | 10/2013 | Peyman |
| 8,568,317 B1 | 10/2013 | Gharib et al. |
| 8,591,431 B2 | 11/2013 | Calancie et al. |
| 8,641,638 B2 | 2/2014 | Kelleher et al. |
| 8,731,654 B2 | 5/2014 | Johnson et al. |
| 8,784,330 B1 | 7/2014 | Scholl et al. |
| 8,792,977 B2 | 7/2014 | Kakei et al. |
| 8,855,822 B2 | 10/2014 | Bartol et al. |
| 8,864,654 B2 | 10/2014 | Kleiner et al. |
| 8,936,626 B1 | 1/2015 | Tohmeh et al. |
| 8,945,004 B2 | 2/2015 | Miles et al. |
| 8,958,869 B2 | 2/2015 | Kelleher et al. |
| 8,982,593 B2 | 3/2015 | Nondahl et al. |
| 8,989,855 B2 | 3/2015 | Murphy et al. |
| 8,989,866 B2 | 3/2015 | Gharib et al. |
| 9,014,776 B2 | 4/2015 | Marino et al. |
| 9,014,797 B2 | 4/2015 | Shiffman et al. |
| 9,037,250 B2 | 5/2015 | Kaula et al. |
| 9,066,701 B1 | 6/2015 | Finley et al. |
| 9,084,550 B1 * | 7/2015 | Bartol ............... A61B 5/0488 |
| 9,084,551 B2 | 7/2015 | Brunnett et al. |
| 9,131,947 B2 | 9/2015 | Ferree |
| 9,192,415 B1 | 11/2015 | Arnold et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,392,953 B1 | 7/2016 | Gharib |
| 9,446,259 B2 | 9/2016 | Phillips et al. |
| 9,622,684 B2 | 4/2017 | Wybo |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0082877 A1 | 4/2004 | Kouou et al. |
| 2004/0186535 A1 | 9/2004 | Knowlton |
| 2004/0230138 A1 | 11/2004 | Inoue et al. |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2006/0276704 A1 | 12/2006 | McGinnis et al. |
| 2007/0038155 A1 | 2/2007 | Kelly, Jr. et al. |
| 2007/0049826 A1 | 3/2007 | Willis |
| 2007/0232958 A1 | 10/2007 | Donofrio et al. |
| 2007/0265675 A1 | 11/2007 | Lund et al. |
| 2007/0276270 A1 | 11/2007 | Tran |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1 | 7/2009 | Schmitz et al. |
| 2009/0192413 A1 | 7/2009 | Sela et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Tran |
| 2010/0137748 A1 | 6/2010 | Sone et al. |
| 2010/0152619 A1 | 6/2010 | Kalpaxis et al. |
| 2010/0152622 A1 | 6/2010 | Teulings |
| 2010/0152623 A1 | 6/2010 | Williams |
| 2010/0168559 A1 | 7/2010 | Tegg et al. |

(56) References Cited

U.S. PATENT DOCUMENTS

| | | |
|---|---|---|
| 2010/0262042 A1 | 10/2010 | Kirn |
| 2010/0292617 A1 | 11/2010 | Lei et al. |
| 2011/0004207 A1 | 1/2011 | Wallace et al. |
| 2011/0230782 A1 | 9/2011 | Bartol et al. |
| 2011/0237974 A1 | 9/2011 | Bartol et al. |
| 2011/0270121 A1 | 11/2011 | Johnson et al. |
| 2011/0301665 A1 | 12/2011 | Mercanzini et al. |
| 2012/0053491 A1 | 3/2012 | Nathan et al. |
| 2012/0191003 A1 | 7/2012 | Garabedian et al. |
| 2013/0197321 A1 | 8/2013 | Wilson |
| 2013/0204097 A1 | 8/2013 | Rondoni et al. |
| 2013/0213659 A1 | 8/2013 | Luyster et al. |
| 2013/0253533 A1 | 9/2013 | Bartol et al. |
| 2014/0020178 A1 | 1/2014 | Stashuk et al. |
| 2014/0066803 A1 | 3/2014 | Choi |
| 2014/0088029 A1 | 3/2014 | Sugimoto et al. |
| 2014/0107524 A1* | 4/2014 | Brull ............... A61B 5/0488 600/554 |
| 2014/0121555 A1 | 5/2014 | Scott et al. |
| 2014/0148725 A1 | 5/2014 | Cadwell |
| 2014/0163411 A1 | 6/2014 | Rea |
| 2014/0275926 A1 | 9/2014 | Scott et al. |
| 2014/0276195 A1 | 9/2014 | Papay et al. |
| 2014/0336722 A1* | 11/2014 | Rocon De Lima ......... A61N 1/36025 607/45 |
| 2014/0358026 A1 | 12/2014 | Mashiach et al. |
| 2015/0032022 A1* | 1/2015 | Stone ............... A61B 5/04001 600/547 |
| 2015/0045783 A1 | 2/2015 | Edidin |
| 2015/0051506 A1 | 2/2015 | Wybo et al. |
| 2015/0112325 A1 | 4/2015 | Whitman |
| 2015/0230749 A1 | 8/2015 | Gharib et al. |
| 2015/0342521 A1 | 12/2015 | Narita et al. |
| 2015/0342621 A1 | 12/2015 | Jackson, III |
| 2016/0051812 A1 | 2/2016 | Montgomery, Jr. et al. |
| 2018/0132757 A1 | 5/2018 | Kong et al. |
| 2019/0223764 A1* | 7/2019 | Hulvershorn ......... A61B 5/7217 |

FOREIGN PATENT DOCUMENTS

| | | |
|---|---|---|
| EP | 2231003 A1 | 9/2010 |
| EP | 2535082 A1 | 12/2012 |
| FR | 2920087 A1 | 2/2009 |
| WO | 0078209 A2 | 12/2000 |
| WO | 2007024147 A1 | 3/2007 |
| WO | 2014160832 A2 | 10/2014 |
| WO | 2015171619 A1 | 11/2015 |
| WO | 2016100340 A1 | 6/2016 |

OTHER PUBLICATIONS

Amini, N., "Accelerometer-based on-body sensor localization for health and medical monitoring applications," Pervasive and Mobile Computing, Sep. 21, 2011.

J. Herdmann MD; V. Deletis MD PHD; H.Edmonds PHD; N. Morota MD, Spinal Cord and Nerve Root Monitoring in Spine Surgery and Related Procedures, Spine Journal, Apr. 1, 1996, pp. 879-885, vol. 21.

N. Hollands MB, BS; J. Kostuik. Continuous Electromyographic Moniotring to Detect Nerve Root Injury During Thoracolumbar Scoliosis Surgery, Spine Journal, Nov. 1, 1997, pp. 2547-2550, vol. 22, Issue 21.

C. Harper, J. Daube, Facial Nerve Electromyography and Other Cranial Nerve Monitoring, Journal of Clinical Neurophysiology, May 1998, pp. 206-216, vol. 15, Issue 3.

D. Beck, J. Ben Ecke JR, Intraoperative Facial Nerve Monitoring Technical Aspects, Official Journal of the American Academy of Otolaryngology—Head and Neck Surgery Foundation, Apr. 27, 1989.

W. Welch MD, R. Rose PHD, J. Balzer PHD, G. Jacobs, MD, Evaluation with evoked and spontaneous electromyography during lumbar instrumentation: a prospective study, Journal of Neurosurgery, Sep. 1997, pp. 397-402, vol. 87, No. 3.

W. Young MD, D. Morledge PHD, W. Martin PHD, K. Park MD, Intraoperative Stimulation of Pedicle Screws: A New Method for Verification of Screw Placement, Journal of Neurosurgery, 1995, pp. 544-547 vol. 44.

K. Sugita MD, S. Kobayashi MD, Technical and instrumental improvements in the surgical treatment of acoustic neurinomas, Journal of Neurosurgery, Dec. 1982, pp. 747-752, vol. 57.

J. Boston, L. Deneault, Sensory evoked potentials: a system for clinical testing and patient monitoring, International Journal of Clinical Monitoring and Computing, 1984, pp. 13-19, Martinus Nijhoff Publishers, Netherlands.

A. Moller, Neuromonitoring in Operations in the Skull Base, The Keio Journal of Medicine, Oct. 1991, pp. 151-159.

J. Maurer, H. Pelster, W. Mann, Intraoperatives Monitoring motorischer Hurnnerven bei Operationen an Hals und Schadelbasis, Laryngo-Rhino-Otol, pp. 561-567, vol. 73.

W. Friedman MD, M. Curran R. EPT, Somatosensory Evoked Potentials after Sequential Extremity Stimulation: A New Method for Improved Monitoring Accuracy, Neurosurgery, 1987, pp. 755-758, vol. 21, No. 5.

R. Gopalan, P. Parker, R. Scott, Microprocessor-Based System for Monitoring Spinal Evoked Potentials During Surgery, IEEE Transactions on Biomedical Engineering, Oct. 1986, pp. 982-985, vol. BME-22, No. 10.

B. Moed MD, B. Ahmad MD, J. Craig MD, G. Jacobson PHD, M. Anders MD, Intraoperative Monitoring with Stimulus-Evoked Electromyography during Placement Iliosacral Screws, The Journal of Bone and Joint Surgery, Apr. 1998, pp. 537-546, vol. 80-A, No. 4, The Journal of Bone and Joint Surgery, Inc.

C. Yingling PHD, J. Gardi PHD, Intraoperative Monitoring of Facial and Cochlear Nerves During Acoustic Neuroma Surgery, Acoustic Neuroma I, Apr. 1992, pp. 413-448, vol. 25, No. 2, Otolaryngologic Clinics of North America.

N. Holland MB, BS, J. Kostuik MD, Continuous Electromyographic Monitoring to Detect Nerve Root Injury During Thoracolumbar Scoliosis Surgery, Spine, 1997, pp. 2547-2550, vol. 22, No. 21, Lippincott-Raven Publishers.

P. Dulguerov, F. Marchal, W. Lehmann, Postparotidectomy Facial Nerve Paralysis: Possible Etiologic Factors and Results with Routine Facial Nerve Monitoring, The Laryngoscope, May 1999, pp. 754-762 vol. 109, Lippincott Williams & Wilkins, Inc. Philadelphia, Pennsylvania.

M. Imai MS, Y. Harada MD, Y. Atsuta MD, Y. Takemitsu MD, T. Iwahara MD, Automated Spinal Cord Monitoring for Spinal Surgery, Paraplegia, 1989, pp. 204-211.

R. Witt, Facial nerve monitoring in parotid surgery: The standard of care?, Otolaryngology—Head and Neck Surgery, Nov. 1998, pp. 468-470, vol. 119, No. 5.

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

(56) References Cited

OTHER PUBLICATIONS

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference Biosignal 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007.

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

\* cited by examiner

NEUROMUSCULAR SENSING DEVICE WITH MULTI-SENSOR ARRAY

TECHNICAL FIELD

The present disclosure relates generally to a sensing device used with a surgical diagnostic system for detecting artificially induced neuromuscular activity.

BACKGROUND

Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

In many surgical procedures, it may be common to include ancillary monitoring devices or therapeutic devices provided around limbs or other anatomy of the subject. Examples may include anti-embolism stockings, sequential compression devices, blood pressure cuffs, anesthesia monitoring devices, and the like. When used, these devices may cover portions of the body and limit access to muscles that may otherwise need to be monitored for the purpose of active nerve detection.

SUMMARY

A neural monitoring system, including a sleeve-like neuromuscular sensing device is provided to detect an artificially-induced mechanical response of a muscle to stimulus provided within an intracorporeal treatment area of a human subject. The intracorporeal treatment area generally includes a nerve that innervates one or more monitored muscles, which are in direct communication with the sensing device.

In an embodiment, the sensing device may include a carrier material and a plurality of mechanical sensors. The carrier material is operative to be secured around a portion of the limb, and each of the plurality of mechanical sensors are coupled with the carrier material. Each mechanical sensor is positioned on the carrier material such that it is operative to monitor a mechanical response of a different muscle group of the limb. Each mechanical sensor then generates a respective mechanomyography output signal corresponding to the monitored mechanical response of its adjacent muscle group. These signals may then be communicated outbound from the device via communication circuitry provided on the device.

The features and advantages and other features and advantages of the present technology are readily apparent from the following detailed description when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
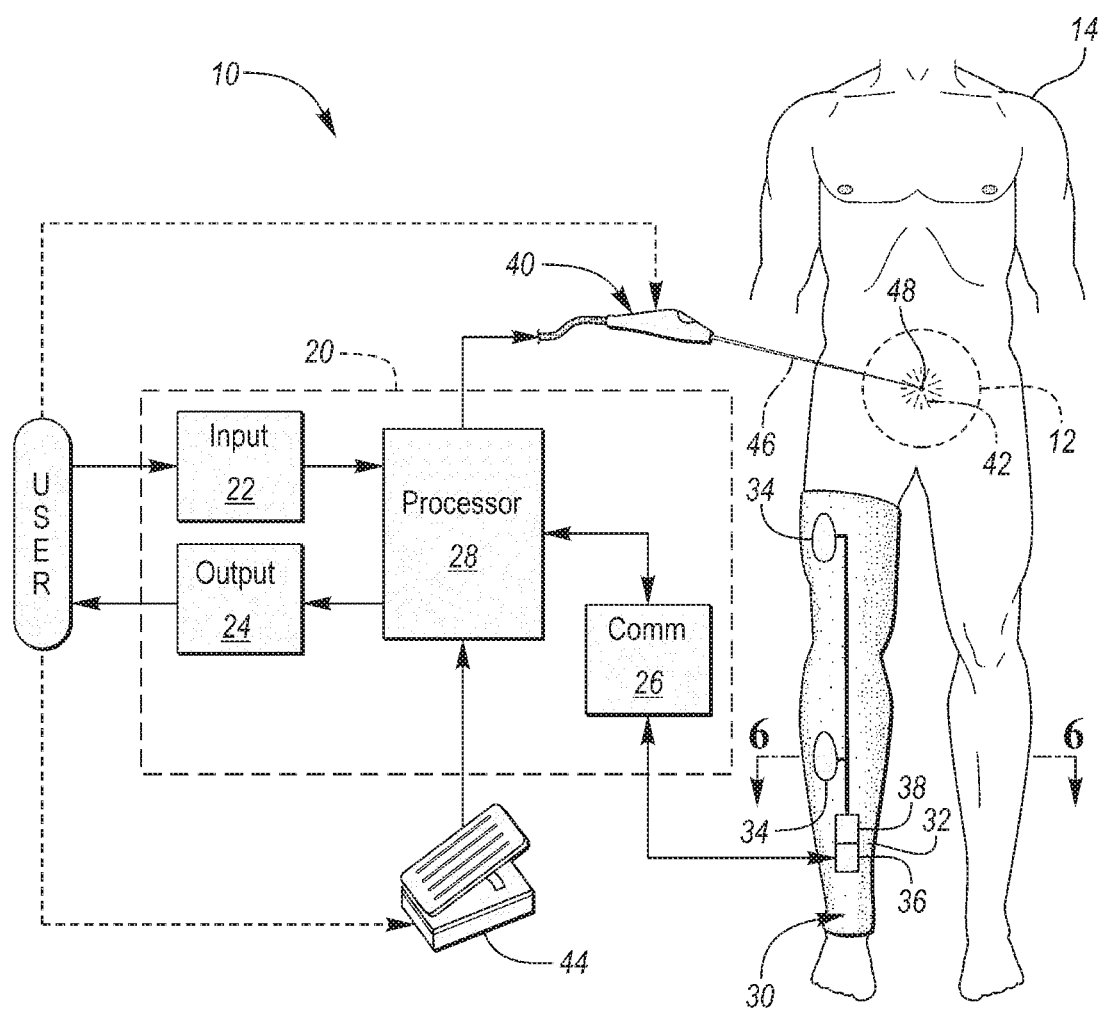
FIG. 1 is a schematic diagram of a neural monitoring system, including a sleeve-based sensing device, for detecting an artificially-induced mechanical muscle response.

The present disclosure provides a sensing device for detecting an artificially induced neuromuscular response of a subject. The device may include an array of neuromuscular sensors that are provided on a carrier material, which is operative to be secured to or around a portion of a limb of the subject. The sensor array may monitor a plurality of muscle groups of the limb, for example, by positioning one or more sensors into contact with the skin of the subject immediately adjacent to the respective muscle group. In most embodiments, each sensor in the array includes a mechanical sensor that is operative to monitor the mechanical motion of the adjacent muscle group. Using various processing techniques, the system may be capable of discerning whether the sensed mechanical motion is representative of an artificially induced muscle response, such as may be caused by an electrical stimulus provided to an innervating nerve. These processing techniques may involve actively filtering out noise, gross motion, and/or signal content outside of an expected response window, while also examining the signal or signals from the sensors for attributes or patterns that are indicative of an induced response. If the processing and event detection is performed locally on the device, then in some embodiments, the sensor device may be capable of transmitting, via the communications circuitry, one or more analog signal traces that are representative of the induced muscle response.

To minimize pre-operative setup while reducing the potential for error, the sensor device may be provided as an integrated unit that may be affixed to the subject by either securing it around the limb (similar to a blood pressure cuff) or by pulling the device onto the subject, such as with anti-embolism stockings. In doing so, the carrier material may locate the array about the subject in a quicker manner than if each sensor was individually placed.

In some embodiments, the sensor device may include onboard processing capabilities and onboard communication circuitry that is operative to transmit one or more alerts or mechanomyography output signals to a host system that is in digital communication with the device. The sensor device may further incorporate ancillary functionality, which eliminates the need for any sensing or therapeutic systems that would otherwise compete with the neuromuscular sensors for space on the subject. Providing an integrated sensing device in this manner minimizes any required pre-operative setup (i.e., one properly located device may serve multiple purposes). Examples of such ancillary functionality may include anesthesia monitoring functionality, thromboembolism-deterrent functionality, blood pressure monitoring functionality, biometric and/or vital monitoring, and the like.

To reduce the potential for improper affixment/positioning on the subject, in some embodiments, the system and/or sensing device may be capable of performing one or more diagnostic routines that investigate whether the device is positioned in the correct orientation about the limb, and whether it is positioned on the correct limb at all. If the device is not properly oriented or positioned on the body, the sensing device may provide an alert, which may inform a surgeon to a potential loss of accuracy in the monitored parameters. In some embodiments, the use of an array of sensors across the limb may provide additional gross motion rejection by more easily identifying a gross translation or rotation of the limb (i.e., if all sensors move in unison, then the sensed motion is not likely induced by the electrical depolarization of a nerve). While it is noted above that ancillary functionality may be included into the sensor device, in some embodiments, the ancillary functionality may rely on the neuromuscular sensors provided in the array to serve a dual purpose and enable the ancillary functionality. An example of this may include depth of anesthesia monitoring, where a Train of Four (ToF) stimulus may be provided to the limb, while the sensors monitor for the response to the ToF stimulus. Similarly, Nerve Conduction Velocity measurements may be performed, in part by examining when different muscle group contractions occur (via the sensor array) in response to a single stimulus.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14, such as during a surgical procedure. As will be described in greater detail below, the system 10 may monitor one or more muscles of the subject 14 for a neuromuscular response that is indicative of a stimulus-induced depolarization of a nerve (i.e., an artificially induced neuromuscular response). If a response of the muscle to the stimulus is detected during the procedure, the system 10 may provide an alert or indication to the surgeon, which may enable the surgeon to take an appropriate action if such action is warranted.

As used herein, an "artificially induced neuromuscular response" is a response of a muscle to a depolarizing stimulus that is applied to a nerve innervating the muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may artificially cause the nerve to depolarize (resulting in a corresponding contraction of the muscle or muscles innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially induced neuromuscular response, a muscle innervated by the artificially depolarized nerve may physically contract or relax (i.e., a mechanical response) and/or the electrical potential throughout the muscle may be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

Figure 2:
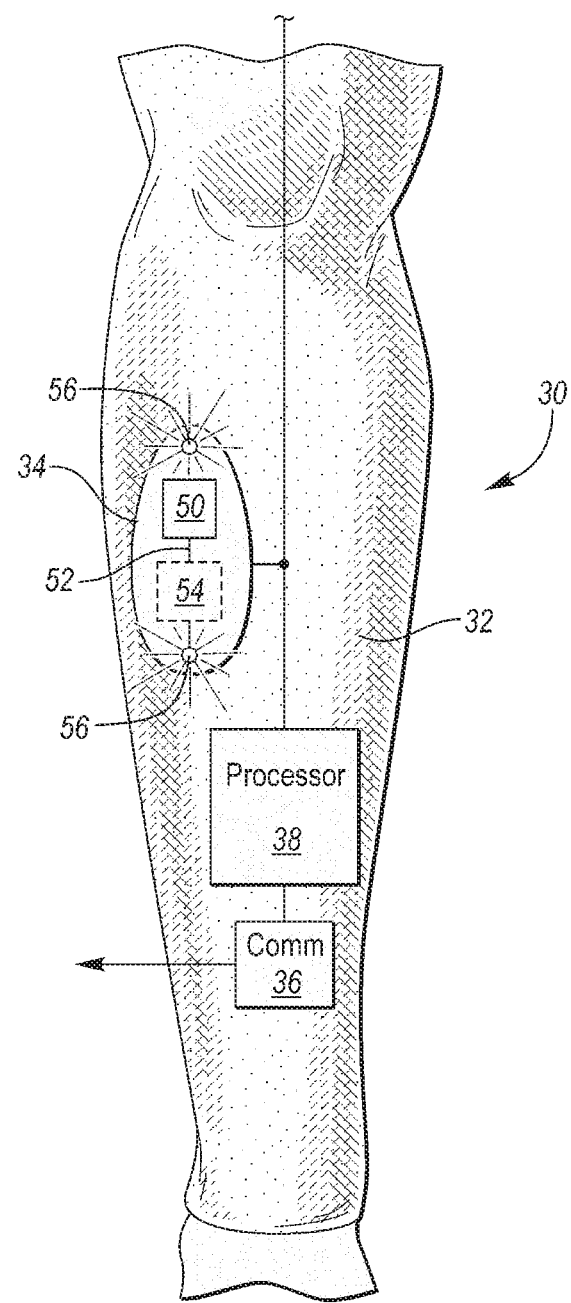
FIG. 2 is an enlarged schematic anterior view of a sleeve-based sensing device provided on a leg of a subject.

The neural monitoring system 10 may generally include a host system 20 and a sensing device 30 that may cooperate to detect a neuromuscular response of a muscle to a stimulus 42 provided by a stimulator 40. As schematically shown in FIG. 2, the host system 20 may include one or more input devices 22 that are operative to receive information from the surgeon, one or more output devices 24 that are operative to communicate alerts or to provide informational feedback to the surgeon, communication circuitry 26 operative to communicate with the sensing device 30, and a processor 28 that is operative to at least manage the flow of information between the input devices 22, output devices 24 and communication circuitry 26.

In general, the one or more input devices 22 may include a keyboard, a mouse, and/or a digitizer provided with a touch-screen display. These devices may receive pre-operative case information or may permit a surgeon to alter various intraoperative parameters, alarm limits, or other case information before or during a procedure. In some embodiments, the stimulator 40 and/or a foot pedal 44 may provide additional input to the host system 20. This input may be in the form of an analog or digital signal that is indicative of the delivery and/or magnitude of a stimulus. The output device 24 may include, for example, a visual display such as an LED/LCD display, one or more indicator lights, or speakers capable of providing an audible alert to the surgeon.

The sensing device 30 is the portion of the system 10 that directly contacts the subject 14 and is responsible for, at a minimum, sensing/detecting neuromuscular responses of the subject 14. The sensing device 30 includes a carrier material 32 that is operative to be secured to the subject 14, and a plurality of neuromuscular sensors 34 that are coupled with the carrier material 32 and each operative to monitor a neuromuscular response of a different muscle group of the subject 14. The sensing device 30 may further include communication circuitry 36 that is operative to digitally communicate with the communication circuitry 26 of the host system 20, and a local processor 38 that is in communication with the plurality of neuromuscular sensors 34 and with the communication circuitry 36. In general, processors used with the present system 10 (e.g., processors 28, 38) may each be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

While the specific nature of the sensing device 30 and carrier material 32 may vary based on the location of the surgical site and nature of the surgical procedure, in many cases the carrier material 32 may resemble a cuff or sleeve that is secured around a limb of the subject. Such a design may be suitable, for example, with a spinal procedure where nerves existing within the surgical site are known to innervate peripheral muscles of the arms or legs.

In some embodiments, the carrier material 32 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 32 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 32 may include, for example, a blood pressure cuff worn around the subject's arm (or else may include functionality similar to that of a standard blood pressure cuff). In these examples, the carrier material 32 serves a function outside of that of a dedicated neuromuscular sensing device, and thus provides efficiencies in pre-op preparation and planning, while also allowing monitoring access on sometimes crowded limbs.

From the perspective of the sensing device 30, the carrier material's main purpose is to hold the neuromuscular sensors 34 in relatively stable contact with the skin of the subject. While the present technology has a beneficial use with electromyography (EMG) (i.e., by ensuring that needle electrodes are held in firm, relative position in the muscle without much risk of falling out), the full functionality of the device 30 is best realized when the neuromuscular sensors 34 are configured to monitor the mechanical responses of the various muscles, or, at a minimum, capable of detecting the static force of gravity. Therefore, while in one embodiment, the neuromuscular sensors 34 are or include EMG electrodes, in a more preferred embodiment, the neuromuscular sensors 34 each include a respective mechanical sensor 50 (such as shown in FIG. 2) that is operative to monitor a mechanical response of a directly adjacent muscle group.

In various embodiments, the mechanical sensor 50 in each neuromuscular sensor 34 may include, for example, a strain gauge, a pressure/force transducer, a position encoder, an accelerometer, a piezoelectric material, or any other transducer or combination of transducers that may convert a physical motion into a variable electrical signal. As will be discussed below, in particular embodiments, the inclusion of an accelerometer or other sensor capable of measuring the direction of a gravitational force may enable diagnostics that may not be possible with other sensors such as electrodes, strain gauges, or pressure mapping meshes/films (e.g., sensors that operate on the basis of monitoring electrical potentials, contact pressures, tensions, or local flexure). In some embodiments where a pressure, tension, or flexure-based mechanical sensor is most appropriate for monitoring the neuromuscular response, an accelerometer may still be included for ancillary diagnostic purposes.

As noted above, the system 10 may further include one or more elongate medical instruments 40 (i.e., stimulators 40) that are capable of selectively providing a stimulus 42 within the intracorporeal treatment area 12 of the subject 14. For example, in one configuration, the elongate medical instrument 40 may include a probe 46 (e.g., a ball-tip probe, k-wire, or needle) that has an electrode 48 disposed on a distal end portion. The electrode 48 may be selectively electrified, at either the request of a user/physician, or at the command of the processor 28, to provide an electrical stimulus 42 to intracorporeal tissue of the subject. In other configurations, the elongate medical instrument 40 may include a dilator, retractor, clip, cautery probe, pedicle screw, or any other medical instrument that may be used in an invasive medical procedure. Regardless of the instrument, if the intended artificial stimulus is an electrical current, the instrument 40 may include a selectively electrifiable electrode 48 disposed at a portion of the instrument that is intended to contact tissue within the intracorporeal treatment area 12 during the procedure.

During a surgical procedure, the user/surgeon may selectively administer the stimulus to intracorporeal tissue within the treatment area 12 to identify the presence of one or more nerve bundles or fibers. For an electrical stimulus 42, the user/surgeon may administer the stimulus, for example, upon depressing a button or foot pedal 44 that is in communication with the host system 20. The electrical stimulus 42 may, for example, be a periodic stimulus that includes a plurality of sequential discrete pulses (e.g., a step pulse) provided at a frequency of less than about 10 Hz, or from about 1 Hz to about 5 Hz, and preferably between about 2 Hz and about 4 Hz. Each pulse may have a pulse width within the range of about 50 µs to about 400 µs. In other examples, the discrete pulse may have a pulse width within the range of about 50 µs to about 200 µs, or within the range of about 75 µs to about 125 µs. Additionally, in some embodiments, the current amplitude of each pulse may be independently controllable.

If a nerve extends within a predetermined distance of the electrode 48, the electrical stimulus 42 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, the impedance between the electrical stimulus and the ground patch, and the magnitude of the stimulus current. In one configuration, a lookup table may be employed by the processor 28 to provide an approximate distance between the electrode and the nerve, given a known stimulus magnitude and a measured mechanical muscle response.

As noted above, each mechanical sensor 50 may be specially configured to monitor a local mechanical movement of an adjacent muscle group of the subject 14. In response to this sensed movement, each respective mechanical sensor 50 may generate a mechanomyography (MMG) output signal 52 that corresponds to the sensed mechanical movement, force, and/or response of the adjacent muscle. The MMG output signal 52 may be either a digital or analog signal, and the sensor 50 may further include any communication circuitry or local processing circuitry 54 that may be required to transmit the MMG output signal 52 (or a suitable representation thereof) to the processor 38 via a wired or wireless communications. In some embodiments, the sensor 34 may further include a local alert capability, such as a lighting module 56 or audible alert module that may operate at the direction of the local processing circuitry 54 or local processor 38.

The communications circuitry 36 of the sensing device 30 may digitally communicate with the communications circuitry 26 of the host system 20 through any suitable wired or wireless communications means. The respective circuitry 26, 36 may permit unidirectional or bidirectional communications, and may be chosen, in part, according to the number of sensing devices 30 are concurrently used during a procedure (noting that many Bluetooth protocols require point-to-point pairing). Suitable wired protocols include I2C, CAN, TCP/IP, while suitable wireless protocols include IEEE 802.11, Bluetooth, ZigBee, NFC, RFiD or the like.

The following description of setup and operation of the sensing device 30 will be made with respect to a lumbar spinal procedure where the sensing device 30 is provided on a leg of the subject 14. It should be appreciated that the specific nature procedure is illustrative, and should not be read as limiting. The following principles of operation can similarly apply to other procedures, such as spinal procedures performed on the cervical spine (e.g., C5-T1—with the sensing device provided on an arm of the subject), or with other such procedures.

Figure 3:
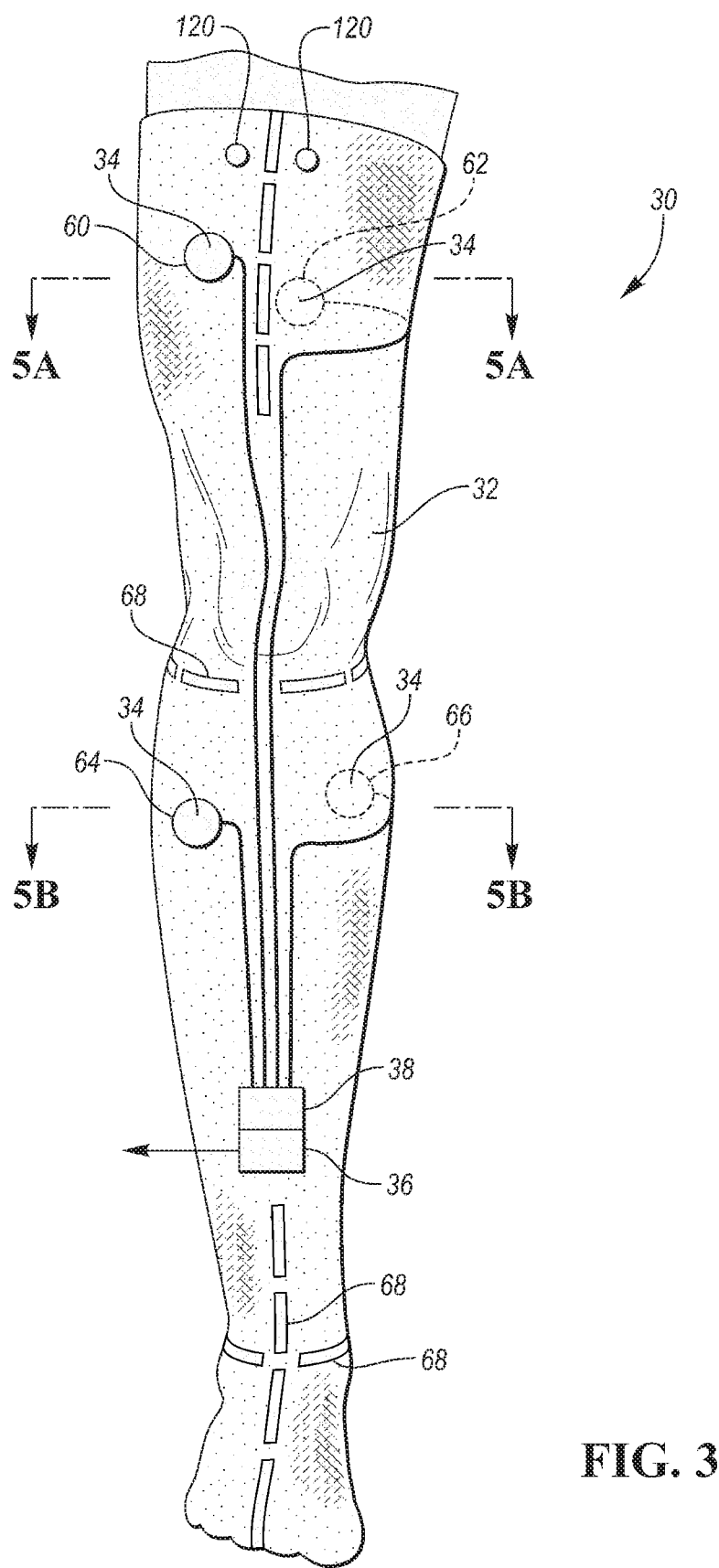
FIG. 3 is an enlarged schematic anterior view of a sleeve-based sensing device provided on a leg of a subject.

FIG. 3 schematically illustrates one embodiment of a sensing device 30 that may be used during the performance of a surgical procedure on the lumbar spine. As shown, the carrier material 32 may be a sleeve that is operative to maintain an elastic tension fit about a leg of the subject. The sensing device 30 includes a plurality of neuromuscular sensors 34 embedded within, or otherwise directly coupled to the carrier material 32. Each sensor 34 is positioned on the carrier material 32 such that it may monitor a response of a different muscle group of the leg. For example, a first sensor 60 may be located on an anterior portion of the thigh, such that it approximately centered above/outward of the vastus lateralis or vastus medialis muscle when the sleeve is properly positioned on the leg of the subject. A second sensor 62 may be located on a posterior portion of the thigh, such that it approximately centered above/outward of the biceps femoris muscle when the sleeve is properly positioned on the leg of the subject. A third sensor 64 may be located on an anterolateral portion of the lower leg, such that it approximately centered above/outward of the tibialis anterior muscle when the sleeve is properly positioned on the leg of the subject. Finally, with some procedures lower on the spine, a fourth sensor 66 may be located on the posterior portion of the lower leg, such that it is approximately centered above/outward of the gastrocnemius muscle when the sleeve is properly positioned on the leg of the subject.

To assist the medical staff in achieving proper alignment of the sleeve on the leg of the subject, the carrier material 32 may include one or more alignment indicia 68 from which relative orientation may be quickly identified. These indicia 68 may include, anatomical markers, such as indications or holes for a knee cap or ankle bone, marks to align with other equipment, marks to align with anatomical reference planes or the like. In one embodiment, the indicia 68 may include a line that extends along a majority of the length of the stocking/sleeve, and/or at certain anatomical waypoints along the length of the limb, such as shown in FIG. 3. In this embodiment, the line(s) may provide a quick visual reference to determine overall relative orientation of the sleeve, while also calling attention to any localized twisting.

In some embodiments, the processor 38 may be configured to use one or more of the mechanical sensors 50 to determine if the sensing device 30 is placed on the correct limb for the given procedure and/or is placed in the proper orientation relative to that limb. In a general sense, this limb/orientation detection functionality relies on an understanding of the nature of the procedure together with an understanding of the static force of gravity acting on the sensor 50.

Figure 4:
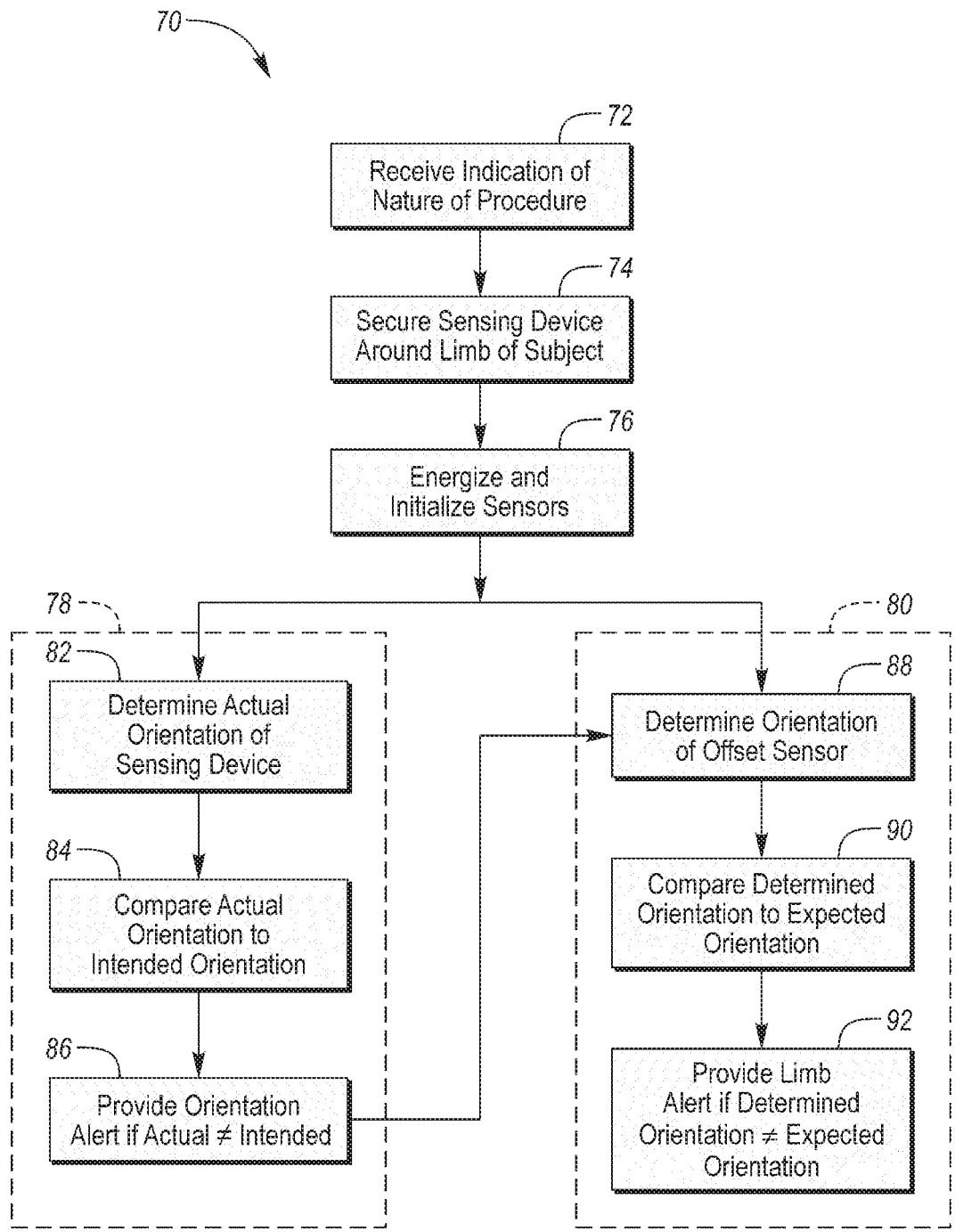
FIG. 4 is a schematic flow diagram for performing pre-operative system diagnostics.

FIG. 4 schematically illustrates an embodiment of limb/orientation algorithm(s) 70 that may be performed by the processor 38. It should be noted that while many of the following electronic processing techniques and/or algorithms are described as being performed via the local sensor device processor 38, unless otherwise noted, in one or more embodiments, each or any of these techniques may be performed by the host processor 28 instead of the sensor device processor 38, or by a combination of the processors 28, 38. Said another way, while in some circumstances, it is beneficial to perform certain processing directly on the device (e.g., to minimize the amount or resolution of data that must be transmitted to the host system 20), in many circumstances, it is largely immaterial which processor performs the technique, and thus the processors 28, 38 should be regarded as extensions of the same processor unless the separation is a material aspect of the algorithm.

As shown in FIG. 4, the limb/orientation algorithm 70 begins by the processor 38 receiving an indication of the nature of the procedure at 72. This indication may include, for example, an indication of the vertebrae or nerve roots within the surgical area, an indication of muscle groups that may be innervated by these nerve roots, an indication of the side of the subject's body where the procedure will be performed, an indication of the type of anesthesia used, and/or an indication of the intended posture of the subject during the procedure. In some embodiments, any or all of this information may be manually input by the surgeon or by the medical staff via the input device 22 associated with the host system 20. In other embodiments, the indication may be downloaded from an electronic medical record or other previously stored record of the procedure.

During this initial setup phase, the sensing device 30 may also be secured around a portion of the limb of the subject 14 (at 74). In this step, it is preferable for the neuromuscular sensors 34/mechanical sensors 50 to each be positioned in contact with or immediately adjacent to the skin above a different muscle group. In doing so, should there be a movement/response of the underlying muscle group, the adjacent sensor 50 would also experience and detect that motion. During this process, any provided alignment indicia 68 should be used to aid in properly orienting the device 30 about the limb.

Each of the plurality of sensors 50 may be energized at 76, after which they may begin generating one or more MMG output signals 52 corresponding to any sensed movement or forces. This step may involve, for example, plugging the sensing device into a power source, flipping a switch (physical or in software), or pulling a barrier tab out of a battery compartment.

Once energized and in place, the processor 38 may then perform one or both of an orientation diagnostic algorithm 78 and/or a limb verification algorithm 80 to ensure that the device 30 is properly positioned and capable of monitoring induced muscle responses should they occur. In a general sense, the orientation diagnostic algorithm 78 may be operative to alert the surgical team if the sensing device might be improperly oriented relative to the subject 14. Likewise, the limb verification algorithm 80 may alert the surgical team if there is a possibility that the sensing device 30 might be positioned on an opposite side of the subject's body from what is intended. Each determination may generally depend on the direction of the force of gravity 100 (shown in FIGS. 5A and 5B), as measured by an accelerometer (or other static force sensor) included with one or more of the neuromuscular sensors 34.

Figure 5A:
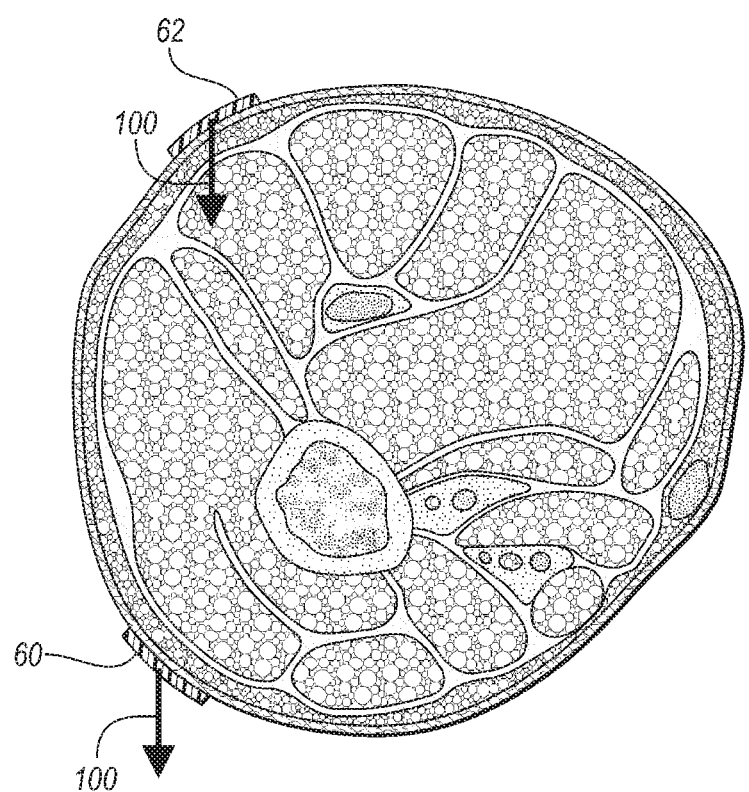
FIG. 5A is a schematic cross-sectional view of a leg, similar to that shown in FIG. 3, and taken through line 5A-5A.
Figure 5B:
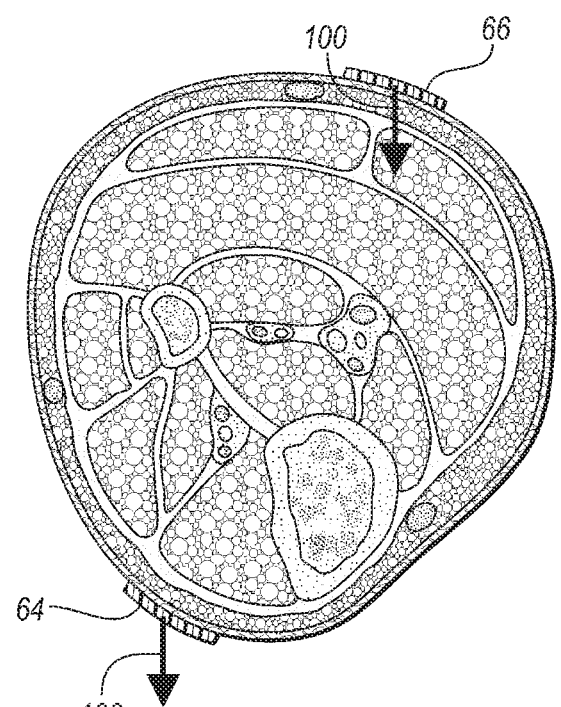
FIG. 5B is a schematic cross-sectional view of a leg, similar to that shown in FIG. 3, and taken through line 5B-5B

The orientation diagnostic algorithm 78 may begin at 82 by determining the actual orientation of the sensing device 30 about the limb. As schematically shown in FIGS. 5A and 5B, the orientation of the sensing device 30 may be determined in a global coordinate frame by examining a static component of one or more MMG output signals 52, i.e., where the static component is representative of the force of gravity 100. Due to variations in the anatomy between subjects, it may be necessary to average a plurality of these static gravity vectors 100 to determine an average ground direction. More specifically, as each sensor 34 will generally lay flush with the subject's skin, the curvature of the body may position each sensor at a different absolute orientation. By knowing the relative positioning of each sensor around the circumference of the carrier material, these absolute orientations for each of the sensors allow the processor to then determine an absolute orientation for the device 30.

As may be appreciated, the MMG output signal 52 may represent the resultant gravity vector 100 as the sum of static forces sensed in multiple orthogonal axes. Calculations may be simplified by orienting the sensing axes such that a first axis is normal to the skin, the second is parallel to a longitudinal axis of the limb, and the last is tangent to a circumference of the limb. In performing the orientation determination, the processor 38 may omit any static gravity component measured in the axis parallel to the longitudinal axis of the limb/sleeve. Doing so would focus the orientation analysis on relative rotation of the sensing device 30 about the limb, and not on limb elevation, which is less relevant for device orientation purposes.

Referring again to FIG. 4, once a global orientation of the device 30 is determined at 82, this orientation may be compared to a proper or intended orientation of the device 30 (at 84). Assuming that subject 14 is in a posture that may be indicated via the nature of the procedure (at 72), the relative orientation of the device 30 should be deemed to be correct if the determined orientation is within a predetermined angular tolerance of the intended orientation. In some embodiments, the orientation determination (at 82) and comparison (at 84) may occur separately at multiple locations along the device 30 (e.g., one around the upper leg—vastus/biceps, and one around the lower leg—tibialis/gastrocnemius). This may allow the processor 38 to recognize any localized twisting.

If the current orientation of the sensing device 30 does not match the intended orientation (within an acceptable tolerance), an alert may be provided (at 86). The alert at 86 may include, for example, a visual or audible alert provided via the output device 24 of the host system 20, or, in some embodiments, may include a light or sound provided directly from the sensing device 30 to indicate misalignment. For example, in one embodiment, the lighting module 56 provided on each sensor 34 (such as shown in FIG. 2) may illuminate a first color if the sensor is misaligned and a second color if it is properly aligned (i.e., if individual gravity vectors are outside of a tolerance from an expected heading). Likewise, in some embodiments, a light may be associated with the processor 38 itself and used to indicate if the average orientation is outside of a tolerance from the expected orientation.

Figure 6:
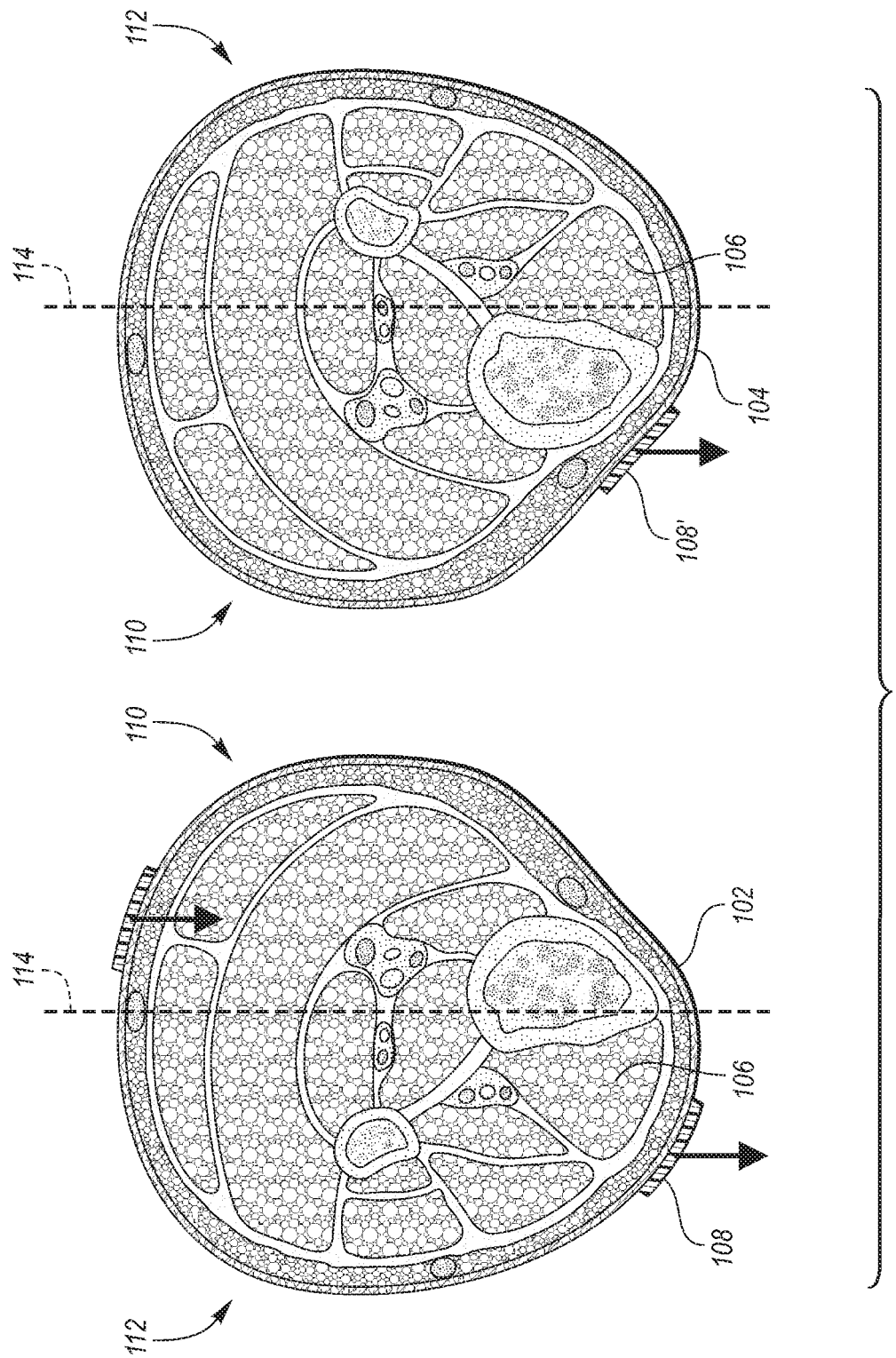
FIG. 6 is a schematic cross-sectional view of the lower legs of a subject, such as shown in FIG. 1, and taken through line 6-6.

Referring again to FIG. 4, the processor 38 may further be configured to perform a limb verification algorithm 80 to determine whether the sensing device 30 is on the proper limb. Improper limb placement, may be the result of inattention during setup, or, for example, inverting left and right sensor devices. The limb verification algorithm 80 relies on the fact that human anatomy is generally mirrored across a bisecting sagittal plane of the body, however limb anatomy is not generally symmetric about a bisecting sagittal plane of the limb. For example, FIG. 6 generally illustrates a cross-section of a subject's left and right legs 102, 104, taken through the tibialis anterior muscle 106. As shown, if the sensing device 30 with sensor 108 was inadvertently placed on the right leg 104 instead of the left leg 102 (with the inadvertent positioning illustrated at 108'), the sensor 108' would be located on the medial side 110 of the leg instead of the lateral side 112. Because the medial and lateral sides 110, 112 of the anterior lower leg are have different surface geometries (i.e., asymmetric about a bisecting sagittal plane 114 of the limb), the sensor 108' would take a different angular orientation against the skin if the sensing device were placed on an incorrect limb. Therefore, in some embodiments, the limb verification algorithm 80 may utilize the limb asymmetries to flag sensors that are at unexpected local orientations.

As shown in FIG. 4, the limb verification algorithm 80 may begin by determining (at 88) the orientation of a sensor 34 that is both offset from a bisecting sagittal plane 114 of the limb, and provided on a portion of the anatomy that is asymmetric about that bisecting sagittal plane. As with the orientation diagnostic algorithm 78, the local orientation of the sensor may be determined by examining static components of the MMG output signal 52, which are indicative of the force of gravity 100.

The processor 38 may then compare this determined sensor orientation with an expected sensor orientation (at 90) to determine whether the sensing device is likely on the correct limb. This comparison may entail one or both of: determining if the sensor orientation is within a predefined angular tolerance of an expected orientation; or estimating both the orientation of the sensor if positioned on the correct limb and if positioned on the incorrect limb, and then determining whether the actual orientation is closer to one or the other. In some embodiments, the expected sensor orientations (for both algorithms 78, 80) may account for variations in the weight of the subject (e.g., via body mass index values) and/or for variations in the actual circumference of the subject's limbs.

If the determined sensor orientation is outside of a predetermined tolerance of the expected heading and/or if it more closely resembles the orientation on the incorrect limb than the correct limb, the processor 38 may provide an alert (at 92) to call attention to the potentially incorrect positioning. Similar to the orientation alert provided at 86, a limb placement alert may be provided by the host system 20, or by one or more lights or speakers associated with the sensing device 30.

In general, the orientation detection algorithm 78 may be most useful for compression sleeves that are generally radially symmetric and/or that do not have provisions for a subject's foot. Limb verification is useful regardless of the symmetry of the device, though it is preferable (though not strictly necessary) for the limb verification algorithms 80 to be performed once the device is properly oriented.

Once the sensing devices are properly positioned on the subject 14, the system 10 may generally operate by applying a stimulus 42 to an intracorporeal treatment area 12 of the subject 14 via the stimulator 40, and then monitoring the resulting neuromuscular activity to determine the existence of an artificially induced muscle response. Because the key to much of the nerve detection lies in the sensing of muscular responses, it may be beneficial for the system 10 to first understand what type and/or magnitude of a response the muscle may be capable of producing prior to beginning the procedure. Understanding a subject's specific response profile may be particularly useful with subjects that have a history of diabetes or neurodegenerative conditions, that have excess subcutaneous fat which may dampen a response or otherwise complicate accurate sensor placement, or that have a general lack of muscle tone/conditioning. In some embodiments, the results from these pre-op muscle diagnostics may be used to scale future responses as a percentage of a maximum possible response, understand approximately the minimum stimulus needed to evoke a response, and/or understand how the magnitude of a muscle response may vary as a function of an applied stimulus.

To perform the pre-op muscle diagnostics, the sensing device 30 may include at least a pair of transdermal surface electrodes 120 (shown in FIG. 3) that are operative to apply an electrical stimulus to the skin of the subject 14. In an embodiment, these surface electrodes 120 may be coupled with the carrier material 32 such that they are held in direct contact with an outer skin surface of the subject when the carrier material 32 is secured around the subject's limb. In some embodiments, the surface electrodes 120 may include a conductive gel that may form the skin-contacting surface of the respective electrodes 120. In one configuration, the electrodes 120 may operate in a bi-polar manner, and may be provided directly over a muscle such that any administered electrical stimulus causes a direct response of the muscle tissue. In another embodiment, however, the electrodes 120 (e.g., bi-polar electrodes) may be placed slightly apart from the muscle, though directly over a nerve that innervates the muscle. For example, in a procedure involving the lumbar spine, the electrodes 120 may be placed directly over the femoral nerve, which innervates the vastus lateralis muscle. Testing the potential response of the muscle to a stimulus applied to the innervating nerve may shed some insight into the health of both the muscle and the nerve downstream of, for example, a spinal impingement.

Figure 7:
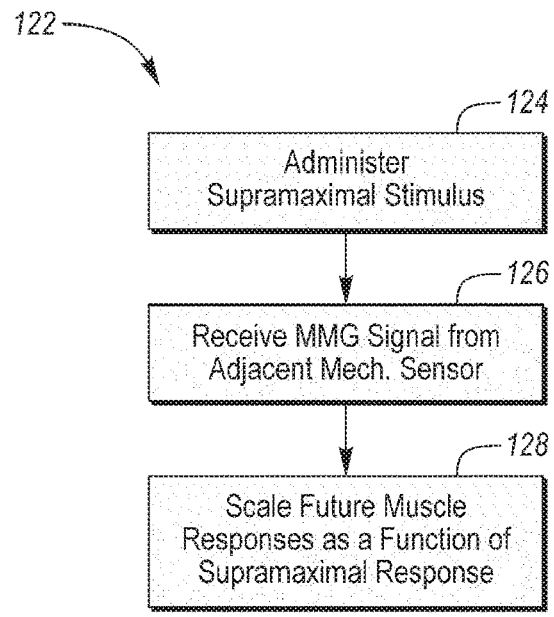
FIG. 7 is a schematic diagram of a method of using incorporated transdermal electrodes to determine a supra-maximal response of a muscle.
Figure 8:
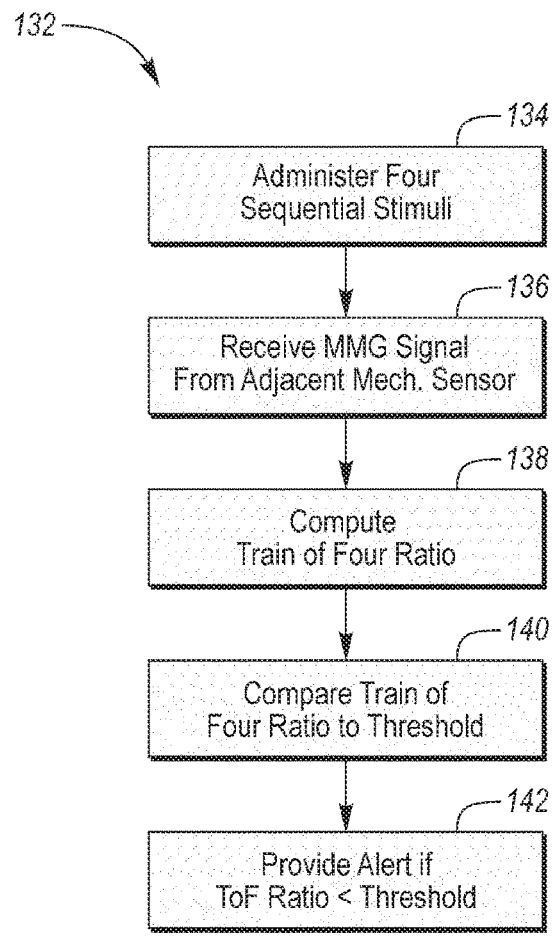
FIG. 8 is a schematic diagram of a method of using incorporated transdermal electrodes and mechanical sensors to estimate the presence of a neuromuscular block during a procedure.

FIGS. 7 and 8 schematically illustrate two methods, 122, 132 for using the transdermal stimulating electrodes 120 provided with the sensing device 30. As shown in FIG. 7, in one configuration the processor 38 may administer an electrical stimulus directly to the limb using the provided electrodes 120 (at 124). In an embodiment, this stimulus may be a supramaximal stimulus that recruits each muscle fiber in the adjacent muscle group to contract. The processor 38 may then receive (at 126) an MMG output signal 52 from the adjacent mechanical sensor 50 that is representative of the supramaximal mechanical response the muscle group to the administered stimulus. Finally, once the maximum possible response is known, any/all future responses of the muscle (e.g., in response to a subsequent stimulus 42 provided by an intraoperative stimulator 40) may be scaled as a function of this response to the administered supramaximal response (at 128).

In a variation of this method 122, the processor 38 may provide a plurality of submaximal electrical stimuli over a period of time, with each submaximal stimulus having a different current magnitude. By monitoring the response to each submaximal stimulus, the processor 38 may then develop a response sensitivity curve that reflects muscle response as a function of transdermal stimulus current. While the numeric relationship between transdermal current and response magnitude may not be directly applicable for stimuli provided within the body (i.e., unless the impedance of the skin was measured prior to testing), the shape of the sensitivity curve may be relevant and used to scale the system's pre-existing understanding of the relationship between stimulus magnitude, response magnitude, and distance between a stimulus and a nerve (i.e., the shape of the response curve may be used to adjust the decay rate of the intraoperative relationships to achieve a better fit given the subject's own neuromuscular anatomy).

FIG. 8 illustrates a method 132 where the pair of electrodes 120 are used to provide a Train of Fours stimulus, from which it may be determined whether the subject 14 has been administered an anesthetic that includes a paralytic or neuromuscular blocking agent. Such agents alter/mute the ability for motor nerves to properly transmit nerve impulses, which could compromise the reliability of the system's nerve detection capabilities. As shown, the method 132 begins by administering four sequential electrical stimuli via the transdermal electrodes 120 (at 134). The processor 38 may then receive (at 136) an MMG output signal 52 from the adjacent mechanical sensor 50, where the output signal 52 is representative of the mechanical response of the muscle group to each administered stimulus.

Following the receipt of the fourth response, the processor 38 may compute a Train of Four ratio (at 138). The Train of Four ratio is computed as the ratio of the amplitude of the MMG output signal 52 in response to the fourth administered electrical stimulus to the amplitude of the MMG output signal 52 in response to the first administered electrical stimulus. The processor 38 may then compare this determined Train of Four ratio to a pre-determined threshold (at 140), and may provide an alert to the user (at 142) if the ratio is below the pre-determined threshold. Similar to the orientation and limb alerts discussed above, the nerve block alert may be provided by the host system 20, or by one or more lights or speakers associated with the sensing device 30.

It should be appreciated that, while the Train of Four analysis is well known in the field of anesthesia monitoring, the present system 10 both integrates this functionality/diagnostic into the existing sensor device 30 (i.e., improved efficiency of setup and sensor positioning) and uses the output to inform the surgeon whether there is an anesthetic that could negatively affect the performance or reliability of the system 10. Incorporation of this functionality eliminates the need for a secondary monitoring system, and uses the results of the test for a purpose outside the field of anesthesiology. Furthermore, incorporation of Train of Four diagnostics leverages the existing sensors 34 to minimize the need for redundant sensing.

In situations where the neuromuscular sensor 34 is or includes a mechanical sensor 50, the artificially induced muscle responses may occur against a background of potentially unrelated limb motion, such as procedure related motion, inadvertent bumps into the operating table, or other such environmental or intentional mechanical noise. Therefore, to properly analyze the MMG output signals 52 and determine the occurrence and magnitude of the induced muscle response, it may be desirable to filter the MMG output signals 52 to remove or attenuate signal content that is indicative of a gross translation or rotation of the limb.

In one embodiment, the sensing device 30 may detect gross translations or rotations by virtue of having a plurality of mechanical sensors 50 held in varying positions around the limb by the carrier material 32. More specifically, if each of the plurality of sensors 50 output a respective signal 52 that, when viewed collectively suggests a coordinated translation or rotation (i.e., a global motion rather than a local motion), any signal content specific to that global motion can be digitally removed. To accomplish this motion detection, in one embodiment, each sensor 50 may directly plug into a local processor 38 that may coordinate the received signals in time (e.g., through the use of time-stamps, clock synchronization, or other buffering or signal processing techniques). The processor 38 may then examine the collection of MMG output signals to identify any motion that is common between the sensors or that is otherwise indicative of a gross translation or rotation of the limb. If any such motion is identified, it may be filtered, attenuated, or otherwise removed from each respective output signal 52 prior to the system performing any further analysis.

In some embodiments, the processor 38 may perform this gross motion rejection by mapping each sensor reading to a three dimensional (virtual) solid model of the limb. This mapping may be accomplished by understanding the number and relative placement of the sensors on the device 30, and by mapping the actual sensed motion to corresponding points on a virtual solid model of the limb. In some embodiments, the processor 38 may receive an indication of the subject's anatomy (e.g., body mass index (BMI), limb circumference, or percent body fat) to scale the size and presumed elastic modulus of the virtual solid model. The global motion may then be extracted from the model, for example, by examining the motion of, for example, the centroid of the model or of a rigid body diagram/representation of the limb.

In some embodiments, using a virtual limb model may not only enable gross motion detection by inspecting the motion of the model, itself, but it may also permit virtual sensor points to be dropped on the model, which may provide a more complete/higher resolution picture of how the limb is responding/moving. This better understanding of the limb motion may then enable greater accuracy when detecting the occurrence and magnitude of an artificially neuromuscular response, while serving to reduce the overall noise floor of the system.

In some embodiments, the system 10 may be configured to automatically perform one or more signal processing algorithms or methods (i.e., via processor 28 and/or 38) to determine whether a mechanical movement sensed by the sensing device 30 is representative of an artificially-induced mechanical muscle response or if it is merely a subject-intended muscle movement and/or an environmentally caused movement. These processing algorithms may be embodied as software or firmware, and may either be stored locally on the processor 28, 38, or may be readily assessable by the processor 28, 38.

Figure 9:
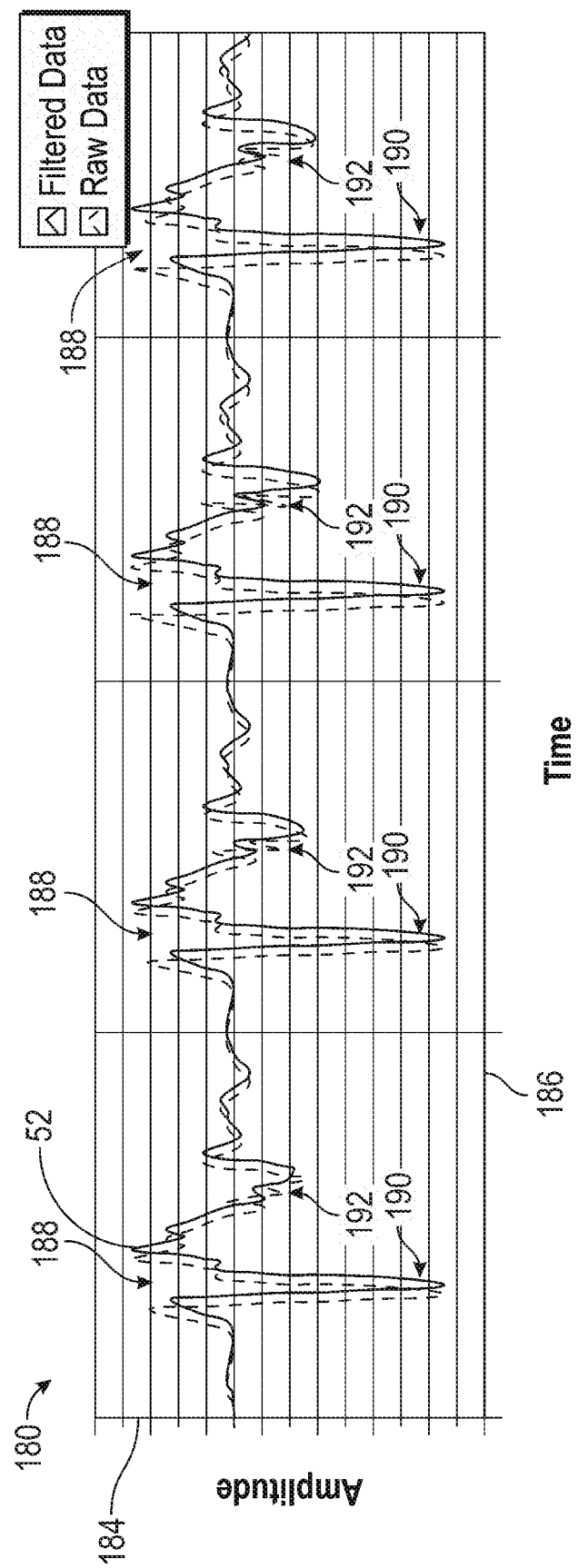
FIG. 9 is a schematic time-domain graph of a mechanomyography output signal in response to a periodic electrical stimulus.

FIG. 9 generally illustrates a graph 180 of an MMG output signal 52 that may be output by one sensor 34 in response to a periodic electrical stimulus 42 provided proximate to a nerve. It should be noted that the graph 180 is provided for illustrative purposes to show a generalized muscular response to a periodic stimulus provided at about a 3 Hz stimulation frequency. As shown, the MMG output signal 52 has an amplitude 184 that varies as a function of time 186 and includes a plurality of generally discrete contraction events 188. Each contraction event 188 may include, for example, an initial response 190 (e.g., an M-wave), and a plurality of subsequent peaks/valleys 192 (e.g., an H-reflex).

Figure 10:
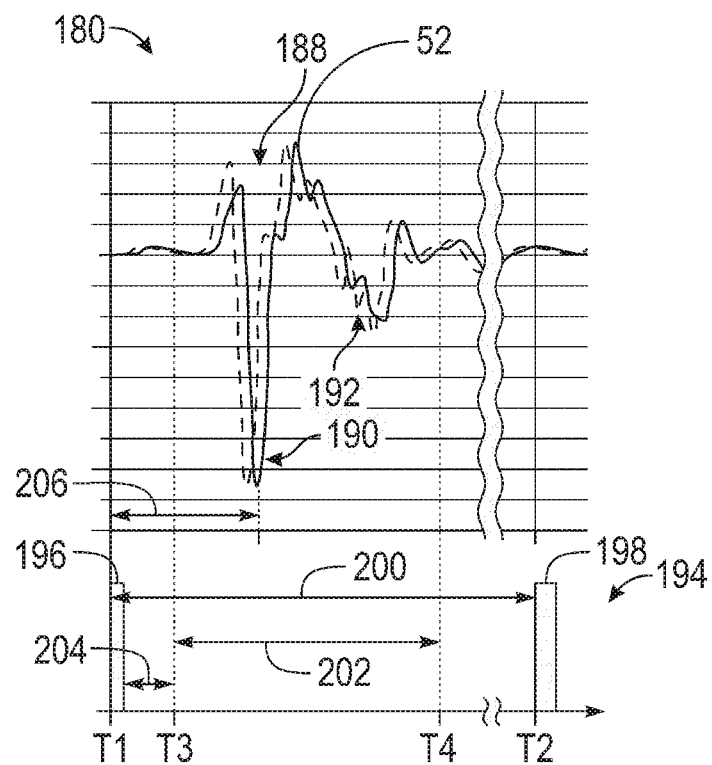
FIG. 10 is a schematic time-domain graph of an induced mechanical response of a muscle within a response window that exists after the application of an inducing stimulus.

FIG. 10 provides an enlarged view of the first event 188 of FIG. 9. In addition to the graph 180 of the MMG output signal 52, FIG. 10 additionally includes a graph 194 representing two consecutive stimuli 196, 198. As generally shown, the first stimulus 196 may be provided by the stimulator 40 beginning at a first time, $T_1$. The second, consecutive stimulus may be provided by the stimulator 40 beginning at a second time, $T_2$. The length of time 200 between $T_1$ and $T_2$ may also be regarded as the period 200 of the periodic stimulus 42. This period 200 may typically be between about 100 ms and 1000 ms, or more typically between about 250 ms and about 500 ms. Within the length of time 200 following the first stimulus 196, there may be a narrower window of time where a muscle event 188 is most likely to occur in response to the first stimulus 196 (i.e., the "response window 202"). The response window 202 generally begins at a time $T_3$ that is on or shortly after $T_1$ and that may represent the earliest time where a response of the muscle to the stimulus could be expected. Likewise, the response window 202 generally ends at a time $T_4$ that is before the next stimulus 198 begins and that provides a large enough period of time from $T_3$ to include at least the entire initial response 190, if one were to occur.

The offset 204 between $T_1$ and $T_3$, if one were to exist would be minimal, as the delay between stimulation and the initial muscle response 190 is only limited by the speed at which the nerve signal propagates, the length of the nerve, and the dynamics of the muscle to actually contract in response to the nerve signal. In most patients, motor nerves can conduct generally between about 40 m/s and about 80 m/s, which could result in about a 5-20 ms delay until the start of the muscular contraction. In some embodiments, the start time $T_3$ of the response window 202 could be further refined by accounting for specific attributes of the patient, such as body mass index (BMI), diabetes, neuropathy, degenerative nerve conditions, or other such factors that are known to affect nerve conduction velocity and/or muscular response.

The relative location of $T_4$ within the period 200 may generally be selected such that if a muscle event 188 were to occur in response to the first stimulus 196, a sufficient amount of information related to the event would fall within the response window 202 to properly categorize it as an induced/evoked muscle response. This later bound may generally depend on the amount of time 206 between $T_1$ and the initial onset and/or peak of the muscle response, as well as on the expected duration of the event 188. From a clinical perspective, it is most important that $T_3$ and $T_4$ are selected to capture at least the initial M-wave response 190 within the response window 202. Similar to $T_3$, the offset of $T_4$ relative to $T_1$ may be further refined by accounting for specific attributes of the patient, such as body mass index (BMI), diabetes, neuropathy, degenerative nerve conditions, muscle fatigue, or other such factors that are known to affect nerve conduction velocity and/or muscular response.

Properly sizing the response window 202 within the period 200 between the stimuli may enable the processor to summarily reject some muscle events (or other detected movements) if those events occur outside of the expected response window 202. Such an analysis may be performed separately for each sensor/sensor channel as a threshold inquiry into whether signal content is representative of a stimulus-induced response. As an example, if a periodic stimulus was applied to a subject at a frequency of 2 Hz (500 ms period), any given pulse may be expected to elicit a response within about the first 100 ms of the onset of the pulse (i.e., with slight variability based on the health of the patient). If a purported muscle event 188 was detected in the later 400 ms of the period 200, it may be safe to assume that the applied stimulus did not cause that motion.

Using these assumptions, in one embodiment, the processor may be configured to only perform the signal processing algorithms on sensed motion or candidate muscle events (i.e., muscle responses that either exceed a certain response amplitude threshold, or have some other time or frequency domain characteristic that is indicative of induced responses), that occur within the response window 202. Such a time-gating filter may reduce the total number of candidate events that must be analyzed, which may conserve processing power, improve processing speed, and reduce the potential for false positives. As mentioned above, the response window should be sized such that $T_1 \leq T_3 < T_4 < T_2$, however, to best realize the processing improvements, it is preferable for $(T_4-T_3) \leq (T_2-T_1)/2$.

In one configuration, the processor may determine the administration of the stimulus (i.e., $T_1$) by either digitally communicating with the stimulator 40 to identify the timing of stimulus 42 (i.e., by digitally directing the stimulator 40 to energize, or by receiving an indication that a stimulus 42 has been administered), or by more directly providing the electrical stimulus energy to the electrode 48. In some embodiments, however, the stimulator 40 may be a stand-alone device that lacks any direct connection or communication with the sensing device 30. In such an embodiment, the sensing device 30 may still be capable of recognizing the occurrence of the stimulus by monitoring changes in one or more electrical parameters of the subject. More specifically, when an electrical stimulus is applied to the body, the electrical potential of all tissue within the body may momentarily change. When monitored in an electromyography context, such an inrush is generally referred to as a stimulus artifact. While a stimulus artifact is generally viewed as a negative quality (i.e., it can complicate electromyography measurements and potentially obscure changes in the muscle action potential), when used with MMG, the stimulus artifact may provide a near real-time indication that a stimulus has been administered.

Therefore, in one embodiment, such as shown in FIG. 3, the electrodes 120 in communication with the processor 38 may be used for the purpose of monitoring one or more electrical parameters of the subject 14 to identify the occurrence of a an electrical stimulus 42. The processor 38 may make this identification by recognizing a momentary change in one or more of the monitored parameters, such as voltage between the electrodes (i.e., evidence of a stimulus artifact). To accomplish this monitoring, the electrodes 120 may include any combination of skin-applied transdermal electrodes and invasive needle electrodes. For example, in one embodiment the pair of electrodes 120 may include two spaced transdermal electrodes held in contact with the skin of the subject 14. In another embodiment the pair of electrodes 120 may include one needle electrode extending through the skin, and one transdermal electrode. Finally, in one embodiment, the pair of electrodes 120 may include two spaced needle electrodes.

In some embodiments, the processor may be configured to perform the signal processing algorithms on sensed motion or candidate muscle events if any one of the plurality of sensors experiences motion or a candidate event within the response window. For example, the MMG output signal on each sensor channel may be recorded in a sliding window/circular buffer until any one channel experiences motion that may be characteristic of a muscular response. At that point, the circular buffer and/or any subsequently received signals for every channel may be stored in an analysis buffer where they may be analyzed individually or collectively to determine whether the candidate motion is representative of an artificially induced response of the muscle.

In some embodiments, the signal processing algorithms used to recognize an induced response may involve one or more analog detection techniques such as described, for example, in U.S. Pat. No. 8,343,065, issued on Jan. 1, 2013 (the '065 patent), which is incorporated by reference in its entirety, and/or one or more digital detection techniques, such as described in US 2015/0051506, filed on Aug. 13, 2013 (the '506 application), which also is incorporated by reference in its entirety. In the analog techniques, the processor may examine one or more aspects of the MMG output signal 52 in an analog/time domain to determine if the sensed response is an artificially-induced response of the muscle to the stimulus. These analog aspects may include, for example, the time derivative of acceleration, or the maximum amplitude of the M-wave/initial response 190.

In a digital context, such as described in the '503 application, the processor may compare the frequency components of the MMG output signal (i.e., in the frequency domain) with the frequency of the applied stimulation to determine whether the sensed muscle responses and/or "events" were induced by the applied stimulus. Such a technique may be made more robust by considering only events or muscle activity that occurs within the reference window 202 and/or by aggressively filtering/attenuating or ignoring the signal outside of the response window 202 prior to applying the signal processing algorithms.

In some embodiments, the signal processing algorithms may include one or more supervised learning algorithms that are operative to classify any sensed motion into one of a plurality of classifications that include at least whether the motion is, or is not representative of an artificially-induced mechanical response of the muscle. Both classifications may provide valuable information to an operating surgeon during a procedure. Affirmatively detecting a response informs the surgeon that a nerve is proximate to the stimulator/tool, and to proceed with caution. Conversely, determining that no induced response occurred, particularly if a stimulus is provided, informs the surgeon that the nerve is not present and they can proceed in their normal manner.

In a general sense, a supervised learning algorithm is an algorithm that attempts to classify a current sample using observations made about prior samples and their known classifications. More specifically, the algorithm attempts to construct and/or optimize a model that is capable of recognizing relationships or patterns between the training inputs and training outputs, and then the algorithm uses that model to predict an output classification given a new sample. Examples of supervised learning algorithms that may be employed include neural networks, support vector machines, logistic regressions, naive Bayes classifiers, decision trees, random forests, or other such techniques or ensembles of techniques.

Figure 11:
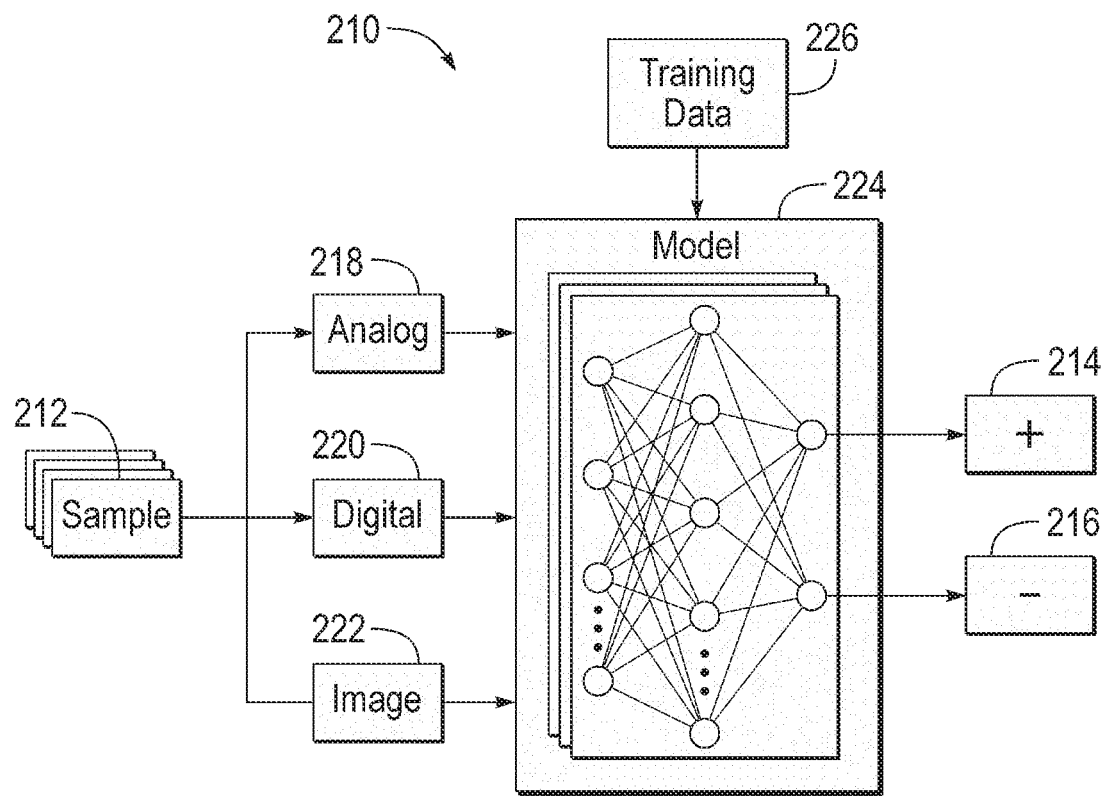
FIG. 11 is a schematic diagram of a signal processing algorithm, including a supervised learning algorithm, for classifying a sensed muscle motion as being either an induced response or not an induced response.

FIG. 11 schematically illustrates an embodiment of a supervised learning algorithm 210 that may be used to classify one or more current samples 212 of MMG output signals 52 into a binary classification (i.e., an artificially induced muscle response 214, or not an artificially induced response 216). While the supervised learning algorithm 210 may certainly be applied on a sensor-by-sensor basis (which may aid in classifying the output from any one sensor channel), in one embodiment, the algorithm 210 may consider the MMG output signals 52 from a plurality of the sensors 34, collectively (e.g., within the analysis buffer as described above). Such a strategy may recognize that a muscle response on a first side of the limb may cause a detectable response in one or more sensors located apart from that muscle by virtue of wave propagation and/or via the dynamics of the limb itself. Furthermore, nerve roots and nerve bundles often serve to innervate multiple muscle groups, though each to varying degrees. Thus, one manner of detecting the induced depolarization of a nerve is to examine the coordinated responses of all muscles the stimulated nerve innervates. Such a multi-channel analysis is generally well suited for supervised learning algorithms.

With continued reference to FIG. 11, the processor may initially characterize the one or more MMG output signals 52/samples 212 and/or any recognized muscle motion according to one or more analog characteristics 218, frequency characteristics 220, and/or time-series/image characteristics 222. The processor may then use a model 224 constructed and/or optimized on the basis of a plurality of pre-classified training samples 226 to make an informed classification that minimizes an established error function or maximizes the probability of an accurate prediction.

In an embodiment, the one or more analog characteristics 218 may include, for example, max/min acceleration amplitudes, max/min velocity amplitudes, time derivative of acceleration, signal rise time, or curve fitting coefficients. Likewise, the one or more frequency characteristics 220 may include, for example, FFT coefficients, peak frequencies, peak frequency magnitudes, harmonic frequencies, or frequency fall-off. Finally, the time-series/image characteristics 222 may include a snapshot of a graph of the MMG output 52 over time (similar to what is shown in FIG. 10). In general, as discussed in the '065 patent and in the '506 application, artificially-induced muscle responses have certain analog and frequency characteristics that non-induced responses do not. As such, the supervised learning algorithm 210 may model these characteristics 218, 220 in the aggregate to predict the nature of the muscle event with a greater accuracy. Furthermore, in some situations, the visual attributes of an induced response may tell a more complete story than any one parameter or collection of parameters could. As such, in an embodiment, the supervised learning algorithm 210 may include an image based classifier that may attempt to classify a muscle response on the basis of a visual similarity with other previously identified induced responses.

In some embodiments, the supervised learning algorithm 210 may employ an ensemble approach to generating the output classification. In such an approach, the model 224 may include a plurality of different models/approaches that may be combined according to a weighting/costing formula to provide improved redundancy/voting. In another embodiment, the ensemble approach may use the output of one or more approaches/models as an input of another model. For example, the analog and/or frequency based detection techniques discussed in the '065 patent and/or in the '506 application may output a probability or likelihood that an event in question is representative of an induced response. These estimations may then be fed into, for example, a supervised learning algorithm as another input (i.e., where the supervised learning algorithm may understand situations when the pre-determined algorithms are to be trusted or not trusted). In another embodiment, each model, including any supervised learning algorithm may feed into a separate algorithm that may output a binary response or probability based upon the outcomes of the various models. This approach may use voting algorithms, probability combinations, and/or separate supervised learning algorithms to provide an output based on the prediction of each constituent model.

In addition to simply detecting an artificially induced muscle response, in an embodiment, the processor may further be configured to examine the timing between a provided stimulus and a muscle response induced by this stimulus. If this timing changes by more than the threshold amount, the processor 28 may provide an alert to a user to indicate a change in the health of the nerve that innervates the responding muscle. As a general premise, nerve conduction velocity and/or muscle response latency should be faster with a healthy nerve than with an injured or impinged nerve.

Figure 12:
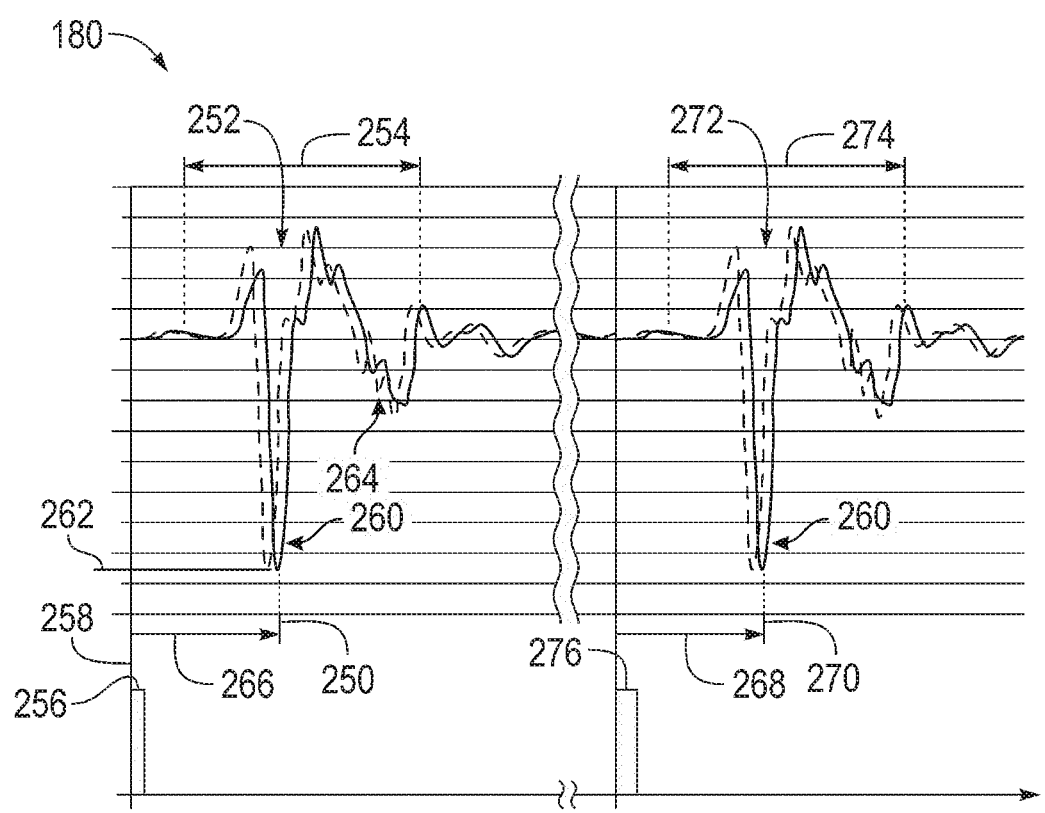
FIG. 12 is a schematic time-domain graph of a technique for comparing a latency between the application of a stimulus and the occurrence of an induced response occurring within a response window.

Therefore, as generally illustrated in FIG. 12, in an embodiment, the processor may be configured to identify a time 250 of a first muscle event 252 that occurs within a first response window 254. The first muscle event 252 is induced by a first stimulus 256 that begins at the first time 258. As generally shown, the muscle event includes an initial M-wave response 260 having a peak magnitude 262, followed by later responses 264 such as the H-reflex. The processor may be configured to determine a first response latency 266 between the first time 256 and the time 250 of the muscle event 252. While it is not critical where the time of the stimulus is recorded, it important that the latency 266 is consistently recorded between measurements. As such, the most optimal times to log the time of the stimulus is on either the rising or falling edge, and the most optimal time to log the time of the event is at the maximum peak (i.e., as peak detection techniques are easily implemented).

Once a baseline latency is established, either by computing a single latency, or an average of many successively computed latencies, future latencies (e.g., subsequent latency 268) may be computed in a similar manner and compared to the baseline. More specifically, the processor may be configured to identify a time 270 of a second muscle event 272 within a second response window 274 following a subsequent stimulus 276 provided by the stimulator. The processor may determine the response latency 268 between the stimulus 276 the second muscle event 272, and may then provide an alert if the second response latency 268 differs from the baseline latency by more than a predetermined threshold amount that is set to indicate either a meaningful improvement in the health of the nerve, or a meaningful impairment of the nerve. Additionally, or alternatively, the system 10 may display a constant readout that compares the nerve conduction velocity and/or muscle response latency to either a baseline level measured from that patient, or to a standard or expected velocity/latency, from which changes throughout the procedure can be gauged.

In yet another embodiment, Nerve Conduction Velocity may be computed by monitoring the difference in time between responses in muscle groups innervated by a common nerve root. For example, the L4 nerve root can innervate both the vastus lateralis and the tibialis anterior muscles. As these muscles are separated a distance along the length of the leg, it should be expected that the tibialis anterior muscle should respond with a slight phase delay. By locally processing these signals, it may be possible to detect this delay, and determine the NCV for at least the portion of the nerve between the two muscles, which may provide insight into the overall health of the nervous system (i.e., since it is unlikely for there to be any impingement between these two muscles which may otherwise affect conduction velocity).

In addition to use as a stand alone, or hand-held nerve monitoring apparatus, the present nerve monitoring system 10 and described artificially-induced mechanical muscle response detection algorithms (as described within method 210) may be used by a robotic surgical system, such as described in U.S. Pat. No. 8,855,622, issued Oct. 7, 2014 entitled "ROBOTIC SURGICAL SYSTEM WITH MECHANOMYOGRAPHY FEEDBACK," which is incorporated by reference in its entirety and for all of the disclosure set forth therein. In such a system, the above-described neural monitoring system 10 may be used to provide one or more control signals to a robotic surgical system if an artificially-induced mechanical muscle response is detected. In such an embodiment, the one or more elongate medical instruments 46 described above may be robotically controlled in up to 6 or more degrees of freedom/motion by a robotic controller. This instrument may be configured to perform a surgical procedure within an intracorporeal treatment area at the direction of the robotic controller, and may provide an electrical stimulus 42 in the manner described above. If an artificially-induced mechanical muscle response is detected, the neural monitoring system 10 may instruct the robotic controller (via the provided control signal) to limit the range of available motion of the elongate medical instrument 46 and/or to prevent an actuation of an end effector that may be disposed on the instrument 46 and controllable by the robotic controller.

While the best modes for carrying out the present technology have been described in detail, those familiar with the art to which this technology relates will recognize various alternative designs and embodiments that are within the scope of the appended claims. It is intended that all matter contained in the above description or shown in the accompanying drawings shall be interpreted as illustrative only and not as limiting.

Various advantages and features of the disclosure are further set forth in the following clauses:

Clause 1: A sensing device for detecting an artificially induced neuromuscular response within a limb of a subject, the sensing device comprising: a carrier material operative to be secured around a portion of the limb; a plurality of mechanical sensors coupled with the carrier material, each mechanical sensor positioned on the carrier material such that it is operative to monitor a mechanical response of a different muscle group of the limb, and wherein each mechanical sensor generates a respective mechanomyography output signal corresponding to the monitored mechanical response, and from which an artificially induced neuromuscular response within the limb can be detected; and communication circuitry coupled with the carrier material and in electronic communication with each of the plurality of mechanical sensors, the communication circuitry operative to transmit one or more of the generated mechanomyography output signals to a host system.

Clause 2: The sensing device of clause 1, wherein the carrier material is a sleeve operative to maintain an elastic tension fit about the limb of the subject.

Clause 3: The sensing device of clause 2, wherein the plurality of mechanical sensors includes a first sensor positioned on the carrier material such that it is directly adjacent to and operative to monitor a mechanical response of at least one the vastus medialis muscle or the vastus lateralis muscle when the carrier material is secured around a portion of the limb in a proper orientation; and wherein the plurality of mechanical sensors includes a second sensor positioned on the carrier material such that it is directly adjacent to and operative to monitor a mechanical response of the tibialis anterior muscle when the carrier material is secured around the portion of the limb in the proper orientation.

Clause 4: The sensing device of any of clauses 1-3 further comprising a processor in communication with the plurality of mechanical sensors.

Clause 5: The sensing device of clause 4, wherein the processor is configured to: receive an indication of the nature of a procedure to be performed on the subject, the nature of the procedure being indicative of a side of the subject's body where the procedure will be performed; receive at least one mechanomyography output signal; identify whether the limb is a right limb or a left limb from a static component of the received mechanomyography output signal; and provide an alert if the limb is not on the side of the subject's body where the procedure will be performed.

Clause 6: The sensing device of any of clauses 4-5, wherein the processor is configured to: receive an indication of an intended posture of the subject during a procedure to be performed on the subject, the intended posture of the subject being indicative of a proper orientation of the sleeve during the procedure; receive at least one mechanomyography output signal; determine an actual orientation of the sleeve from a static component of the at least one mechanomyography output signal; and provide an alert if the actual orientation of the sleeve does not match the proper orientation of the sleeve.

Clause 7: The sensing device of any of clauses 4-6, wherein the processor is in communication with and between the plurality of mechanical sensors and the communication circuitry; and the processor configured to filter each of the mechanomyography output signals to remove signal content that is indicative of a gross translation or rotation of the limb.

Clause 8: The sensing device of clause 7, wherein the processor is configured to identify signal content that is indicative of a gross translation or rotation of the limb by mapping the sensed motion from each of the plurality of sensors to a virtual limb, and determining whether there is a translation or rotation of the virtual limb.

Clause 9: The sensing device of any of clauses 4-8, wherein the processor is configured to: receive an indication that a stimulus has been administered within an intracorporeal treatment area of the subject apart from the limb; analyze each of the mechanomyography output signals to determine whether the stimulus induced a mechanical, neuromuscular response of one or more of the muscle groups within the limb of the subject; and provide an alert if it is determined that the stimulus induced the neuromuscular response.

Clause 10: The sensing device of clause 9, wherein the processor is configured to only analyze each of the mechanomyography output signals within a response window following the administration of the stimulus.

Clause 11: The sensing device of any of clauses 9-10, wherein the processor is configured to determine whether the stimulus induced the mechanical, neuromuscular response of one or more of the muscle groups within the limb of the subject by examining one or more characteristics of one or more received mechanomyography output signals using a supervised learning algorithm; and wherein the supervised learning algorithm is operative to classify the response window into one of a plurality of classifications comprising: the response window is representative of an induced neuromuscular response; and the response window is not representative of an induced neuromuscular response.

Clause 12: The sensing device of any of clauses 9-11, wherein the processor is local to the sensing device and attached to the carrier material; and wherein the communication circuitry is operative to transmit one or more of the generated mechanomyography output signals to the host system only if it is determined that the stimulus induced the neuromuscular response.

Clause 13: The sensing device of any of clauses 9-12, wherein the processor is further configured to determine a nerve conduction velocity by either computing the time delay between the stimulus and a muscle response induced by the stimulus, or by computing the time delay between muscle responses from different muscle groups innervated by a common nerve.

Clause 14: The sensing device of any of clauses 1-13, further comprising: a pair of surface electrodes coupled with the carrier material such that they are operative to directly contact a skin surface of the subject when the carrier material is secured around the portion of the limb; and a processor in electrical communication with the pair of surface electrodes, the processor configured to administer an electrical stimulus directly to the limb via the electrodes.

Clause 15: The sensing device of clause 14, wherein the stimulus is a Train of Four electrical stimulus that includes four discrete electrical pulses; the processor further configured to: monitor the mechanomyography output signal from one of the plurality of mechanical sensors for a mechanical response to each of the four discrete electrical pulses of the Train of Four electrical stimulus; compute a Train of Four ratio from the monitored mechanomyography output signal, the Train of Four ratio being a ratio of an amplitude of the mechanomyography output signal in response to the fourth of the four discrete electrical pulses to an amplitude of the mechanomyography output signal in response to the first of the four discrete electrical pulses; and provide an alert indicative of the existence of a neuromuscular block if the Train of Four ratio is below a predetermined threshold.

Clause 16: The sensing device of any of clauses 14-15, wherein the stimulus is a supramaximal stimulus.

Clause 17: The sensing device of clause 16, wherein the processor is operative to: receive a mechanomyography output signal representative of the mechanical response of a muscle in response to the administered supramaximal stimulus; and scale one or more of the mechanomyography output signals as a function of a magnitude of the mechanical response of the muscle in response to the administered supramaximal stimulus.

Clause 18: The sensing device of any of clauses 1-17, wherein the carrier material is an anti-embolism stocking.

Clause 19: The sensing device of clause 18, wherein the anti-embolism stocking includes one or more alignment indicia to indicate the proper orientation of the stocking relative to the limb.

Clause 20: The sensing device of clause 19, wherein the alignment indicia is a line extending along a majority of the length of the stocking, the line operative to indicate twisting of the stocking when worn by the subject.

Clause 21: The sensing device of any of clauses 1-20, wherein the communication circuitry is wireless digital communications circuitry; and wherein the wireless digital communications circuitry is operative to transmit the one or more generated mechanomyography output signals to the host system via a wireless communications protocol.

Clause 22: A sensing device for detecting an artificially induced neuromuscular response within a limb of a subject, the sensing device comprising: a sensor array comprising a plurality of mechanical sensors, each sensor operative to monitor a mechanical response of a different muscle group of the limb and generate an output signal corresponding to the monitored response; and a processor in communication with the sensor array, the processor configured to receive the output signal from each sensor in the sensor array and to determine if any one or more output signal is indicative of an artificially induced neuromuscular response.

Clause 23: The sensing device of clause 22, further comprising a carrier material operative to be secured around a portion of the limb, and wherein each sensor in the sensor array is coupled with the carrier material.

Clause 24: The sensing device of clause 23, wherein the carrier material is operative to maintain an elastic tension fit about the limb of the subject.

Clause 25: The sensing device of any of clauses 23-24, wherein the carrier material is an anti-embolism stocking configured to be secured around a leg of the subject.

Clause 26: The sensing device of any of clauses 23-24, wherein the carrier material is a compression sleeve operative to be secured around an arm of the subject.

Clause 27: The sensing device of clause 26, wherein the compression sleeve further includes a blood pressure cuff/sphygmomanometer.

Clause 28: The sensing device of clause 27, wherein the processor is operative to determine a blood pressure of the subject via selective actuation and/or inflation of the blood pressure cuff together with monitoring of at least one of the sensors in the sensor array.

Clause 29: The sensing device of any of clauses 23-28, further comprising a bipolar transdermal electrical stimulator including at least two electrodes coupled with the carrier material, the electrodes positioned such that each electrode contacts the skin of the subject when the carrier material is secured around the portion of the limb; and wherein the bipolar stimulator is operative to receive and electrically conduct an electrical stimulus from the processor to the subject via the electrodes.

Clause 30: The sensing device of clause 29, wherein the electrical stimulus is a Train of Four electrical stimulus that includes four discrete electrical pulses; the processor further configured to: monitor the output signal from one of the plurality of mechanical sensors for a mechanical response to each of the four discrete electrical pulses of the Train of Four electrical stimulus; compute a Train of Four ratio from the monitored mechanomyography output signal, the Train of Four ratio being a ratio of an amplitude of the mechanomyography output signal in response to the fourth of the four discrete electrical pulses to an amplitude of the mechanomyography output signal in response to the first of the four discrete electrical pulses; and provide an alert indicative of the existence of a neuromuscular block if the Train of Four ratio is below a predetermined threshold.

Clause 31: The sensing device of any of clauses 29-30, wherein the electrical stimulus is a supramaximal stimulus.

Clause 32: The sensing device of clause 31, wherein the processor is operative to: receive a mechanomyography output signal representative of the mechanical response of a muscle in response to the administered supramaximal stimulus; and scale one or more subsequent mechanomyography output signals as a function of a magnitude of the mechanical response of the muscle in response to the administered supramaximal stimulus.

Clause 33: The sensing device of any of clauses 22-32, wherein the processor is configured to: receive an indication of the nature of a procedure to be performed on the subject, the nature of the procedure being indicative of a side of the subject's body where the procedure will be performed; identify whether the limb is a right limb or a left limb from a static component of a received sensor output signal; and provide an alert if the limb is not on the side of the subject's body where the procedure will be performed.

Clause 34: The sensing device of clause 33, wherein the processor is configured to identify whether the limb is a right limb or a left limb from an orientation of the sensor generating the output signal relative to a vector heading of the static component of the output signal, and wherein the static component is indicative of gravity.

Clause 35: The sensing device of clause 34, wherein the sensor generating the output signal is provided on a portion of the limb where the outer skin surface is asymmetric about a bisecting reference plane.

Clause 36: The sensing device of any of clauses 22-35, wherein the processor is configured to: receive an indication of an intended posture of the subject during a procedure to be performed on the subject, the intended posture of the subject being indicative of a proper orientation of the sleeve during the procedure; determine an actual orientation of the sleeve from a static component of the at least one received output signal; and provide an alert if the actual orientation of the sleeve does not match the proper orientation of the sleeve.

Clause 37: The sensing device of clause 36, wherein the static component of the at least one received output signal is indicative of the force of gravity; and wherein the processor is configured to determine the actual orientation of the sleeve relative to the vector heading of the sensed force of gravity.

Clause 38: The sensing device of any of clauses 36-37, wherein the static component of the received output signal only includes a force magnitude in a direction normal to a skin surface of the subject and in a direction tangential to a circumference of the limb.

Clause 39: The sensing device of any of clauses 36-38, wherein the processor is configured to determine the actual orientation of the sleeve by averaging a vector heading of the static component of a plurality of output signals.

Clause 40: The sensing device of any of clauses 33-39, wherein the alert includes at least one of a visual alert and an audible alert.

Clause 41: The sensing device of any of clauses 22-40, wherein the processor is configured to filter each of the output signals to remove signal content that is indicative of a gross translation or rotation of the limb.

Clause 42: The sensing device of clause 41, wherein the processor is configured to: identify signal content that is indicative of a gross translation or rotation of the limb by mapping the sensed motion from each of the plurality of sensors to a virtual limb, and determining whether there is a translation or rotation of the virtual limb.

Clause 43: The sensing device of any of clauses 22-42, wherein the processor is configured to receive an indication that a stimulus has been administered within an intracorporeal treatment area of the subject apart from the limb; analyze each of the output signals to determine whether the stimulus induced a mechanical, neuromuscular response of one or more of the muscle groups within the limb of the subject; and provide an alert if it is determined that the stimulus induced the neuromuscular response.

Clause 44: The sensing device of clause 43, wherein the processor is configured to only analyze each of the output signals within a response window following the administration of the stimulus.

Clause 45: The sensing device of any of clauses 43-44, wherein the processor is configured to analyze each of the output signals within the response window only if one or more of the output signals have a response magnitude that exceeds a threshold within the response window.

Clause 46: The sensing device of any of clauses 43-45, wherein the processor is configured to determine whether the stimulus induced the mechanical, neuromuscular response of one or more of the muscle groups within the limb of the subject by examining one or more characteristics of one or more received output signals using a supervised learning algorithm; and wherein the supervised learning algorithm is operative to classify a sensed motion into one of a plurality of classifications comprising: the sensed motion is representative of an induced neuromuscular response; and the sensed motion is not representative of an induced neuromuscular response.

Clause 47: The sensing device of any of clauses 43-46, wherein the processor is further configured to determine a nerve conduction velocity by either computing the time delay between the stimulus and a muscle response induced by the stimulus, or by computing the time delay between muscle responses from different muscle groups innervated by a common nerve.

Clause 48: The sensing device of any of clauses 22-47, further comprising communications circuitry in communication with the processor; and wherein the communications circuitry is operative to transmit one or more of the output signals to a host system.

Clause 49: The sensing device of clause 48, wherein the communications circuitry is only configured to transmit the one or more output signals to the host system if the processor detects an artificially induced neuromuscular response within the limb of the subject.

Clause 50: A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising: a host system including a display and a user input; a stimulator configured to provide the stimulus within the intracorporeal treatment area; and the sensing device of any of clauses 1-49.

Clause 51: The neural monitoring system of clause 50, wherein the display is operative to display a trace of one or more of the output signals.

Clause 52: The neural monitoring system of any of clauses 50-51, wherein the host system and sensing device are in wired communication.

Clause 53: The neural monitoring system of any of clauses 50-51, wherein the host system and sensing device are in wireless communication.

Clause 54: The neural monitoring system of any of clauses 50-53, further comprising a second sensing device, the second sensing device according to any of clauses 1-49.

Clause 55: The neural monitoring system of clause 54, where the first sensing device is provided on a first leg of the subject, and wherein the second sensing device is provided on a second leg of the subject.

Clause 56: The neural monitoring system of clause 54, where the first sensing device is provided on a first arm of the subject, and wherein the second sensing device is provided on a second arm of the subject.

The invention claimed is:

1. A sensing device for detecting an artificially induced neuromuscular response within a limb of a subject, the sensing device comprising:
   a carrier material operative to be secured around a portion of the limb;
   a plurality of mechanical sensors coupled with the carrier material, each mechanical sensor positioned on the carrier material such that it is operative to monitor a mechanical response of a different muscle group of the limb, and wherein each mechanical sensor generates a respective mechanomyography output signal corresponding to the monitored mechanical response, and from which an artificially induced neuromuscular response within the limb can be detected; and
   communication circuitry coupled with the carrier material and in electronic communication with each of the plurality of mechanical sensors, the communication circuitry operative to transmit one or more of the generated mechanomyography output signals to a host system; and
   a processor in electrical communication with and between the plurality of mechanical sensors and the communication circuitry, the processor configured to:
      map the sensed motion from each of the plurality of sensors to a virtual limb;
      determine whether there is a translation or rotation of the virtual limb;
      identify signal content that is indicative of a gross translation or rotation of the limb from the virtual limb; and
      filter each of the mechanomyography output signals to remove the identified signal content that is indicative of the gross translation or rotation of the limb.

2. The sensing device of claim 1, wherein the carrier material is a sleeve operative to maintain an elastic tension fit about the limb of the subject.

3. The sensing device of claim 2, wherein the plurality of mechanical sensors includes a first sensor positioned on the carrier material such that it is adapted to be directly adjacent to and operative to monitor a mechanical response of at least one a vastus medialis muscle or a vastus lateralis muscle of the subject when the carrier material is secured around a portion of the limb in a proper orientation; and
   wherein the plurality of mechanical sensors includes a second sensor positioned on the carrier material such that it is directly adjacent to and operative to monitor a mechanical response of the tibialis anterior muscle when the carrier material is secured around the portion of the limb in the proper orientation.

4. The sensing device of claim 1, further comprising a processor configured to:
   receive an indication that a stimulus has been administered within an intracorporeal treatment area of the subject apart from the limb;
   analyze each of the mechanomyography output signals to determine whether the stimulus induced a mechanical, neuromuscular response of one or more of the muscle groups within the limb of the subject; and
   provide an alert when it is determined that the stimulus induced the neuromuscular response.

5. The sensing device of claim 4, wherein the processor is configured to only analyze each of the mechanomyography output signals within a response window following the administration of the stimulus.

6. The sensing device of claim 5, wherein the processor is configured to determine whether the stimulus induced the mechanical, neuromuscular response of one or more of the muscle groups within the limb of the subject by examining one or more characteristics of one or more received mechanomyography output signals using a supervised learning algorithm; and
   wherein the supervised learning algorithm is operative to classify the response window into one of a plurality of classifications comprising:
      the response window is representative of an induced neuromuscular response; and
      the response window is not representative of an induced neuromuscular response.

7. The sensing device of claim 4, wherein the processor is local to the sensing device and attached to the carrier material; and
   wherein the communication circuitry is operative to transmit one or more of the generated mechanomyography output signals to the host system only when it is determined that the stimulus induced the neuromuscular response.

8. The sensing device of claim 4, wherein the processor is further configured to determine a nerve conduction velocity by either computing a time delay between the stimulus and a muscle response induced by the stimulus, or by computing the time delay between muscle responses from different muscle groups innervated by a common nerve.

9. The sensing device of claim 1, wherein the communication circuitry is wireless digital communications circuitry; and
   wherein the wireless digital communications circuitry is operative to transmit the one or more generated mechanomyography output signals to the host system via a wireless communications protocol.

10. The sensing device of claim 1, wherein the processor is further configured to detect an artificially induced neuromuscular response from the filtered mechanomyography output signals.

11. A sensing device for detecting an artificially induced neuromuscular response within a limb of a subject, the sensing device comprising:
   a carrier material operative to be secured around a portion of the limb;
   a plurality of mechanical sensors coupled with the carrier material, each mechanical sensor positioned on the carrier material such that it is operative to monitor a mechanical response of a different muscle group of the limb, and wherein each mechanical sensor generates a respective mechanomyography output signal corresponding to the monitored mechanical response, and from which an artificially induced neuromuscular response within the limb can be detected; and communication circuitry coupled with the carrier material and in electronic communication with each of the plurality of mechanical sensors, the communication circuitry operative to transmit one or more of the generated mechanomyography output signals to a host system; and a processor in communication with the communication circuitry, the processor configured to:
receive an indication of a nature of a procedure to be performed on the subject, the nature of the procedure being indicative of a side of the subject's body where the procedure will be performed;
receive at least one mechanomyography output signal;
identify whether the limb is a right limb or a left limb from a static component of the received mechanomyography output signal; and
provide an alert when the identified limb is not on the side of the subject's body where the procedure will be performed.

12. The sensing device of claim 11, wherein the carrier material is an anti-embolism stocking.

13. A sensing device for detecting an artificially induced neuromuscular response within a limb of a subject, the sensing device comprising:
a carrier material operative to be secured around a portion of the limb;
a plurality of mechanical sensors coupled with the carrier material, each mechanical sensor positioned on the carrier material such that it is operative to monitor a mechanical response of a different muscle group of the limb, and wherein each mechanical sensor generates a respective mechanomyography output signal corresponding to the monitored mechanical response, and from which an artificially induced neuromuscular response within the limb can be detected; and
communication circuitry coupled with the carrier material and in electronic communication with each of the plurality of mechanical sensors, the communication circuitry operative to transmit one or more of the generated mechanomyography output signals to a host system; and
a processor in communication with the communication circuitry, the processor configured to:
receive an indication of an intended posture of the subject during a procedure to be performed on the subject, the intended posture of the subject being indicative of a proper orientation of the sleeve during the procedure;
receive at least one mechanomyography output signal;
determine an actual orientation of the sleeve from a static component of the at least one mechanomyography output signal; and
provide an alert when the actual orientation of the sleeve does not match the proper orientation of the sleeve.

14. The sensing device of claim 13, wherein the carrier material is an anti-embolism stocking.

15. The sensing device of claim 14, wherein the anti-embolism stocking includes one or more alignment indicia to indicate the proper orientation of the stocking relative to the limb.

16. The sensing device of claim 15, wherein the alignment indicia is a line extending along a majority of a length of the stocking, the line operative to indicate twisting of the stocking when worn by the subject.

17. A sensing device for detecting an artificially induced neuromuscular response within a limb of a subject, the sensing device comprising:
a carrier material operative to be secured around a portion of the limb;
a plurality of mechanical sensors coupled with the carrier material, each mechanical sensor positioned on the carrier material such that it is operative to monitor a mechanical response of a different muscle group of the limb, and wherein each mechanical sensor generates a respective mechanomyography output signal corresponding to the monitored mechanical response, and from which an artificially induced neuromuscular response within the limb can be detected; and
a pair of surface electrodes coupled with the carrier material such that they are operative to directly contact a skin surface of the subject when the carrier material is secured around the portion of the limb; and
a processor in electrical communication with the pair of surface electrodes, the processor configured to:
administer a supermaximal electrical stimulus directly to the limb via the electrodes;
receive a mechanomyography output signal representative of the mechanical response of a muscle in response to the administered supramaximal stimulus; and
scale one or more of the mechanomyography output signals as a function of a magnitude of the mechanical response of the muscle in response to the administered supramaximal stimulus.

18. The sensing device of claim 17, wherein the processor is further configured to:
administer a Train of Four electrical stimulus that includes four discrete electrical pulses;
monitor the mechanomyography output signal from one of the plurality of mechanical sensors for a mechanical response to each of the four discrete electrical pulses of the Train of Four electrical stimulus;
compute a Train of Four ratio from the monitored mechanomyography output signal, the Train of Four ratio being a ratio of an amplitude of the mechanomyography output signal in response to the fourth of the four discrete electrical pulses to an amplitude of the mechanomyography output signal in response to the first of the four discrete electrical pulses; and
provide an alert indicative of the existence of a neuromuscular block when the Train of Four ratio is below a predetermined threshold.

* * * * *